United States Patent
Livingston et al.

(10) Patent No.: US 7,399,851 B2
(45) Date of Patent: Jul. 15, 2008

(54) COMPOSITION AND METHOD FOR IMAGING CELLS

(75) Inventors: David M. Livingston, Brookline, MA (US); Andrew L. Kung, Walpole, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 309 days.

(21) Appl. No.: 10/627,075

(22) Filed: Jul. 24, 2003

(65) Prior Publication Data

US 2004/0091913 A1    May 13, 2004

Related U.S. Application Data

(60) Provisional application No. 60/398,583, filed on Jul. 25, 2002.

(51) Int. Cl.
*C07H 21/04* (2006.01)
*C07H 21/02* (2006.01)
*C12N 15/00* (2006.01)

(52) U.S. Cl. .................. 536/24.1; 536/23.1; 435/320.1

(58) Field of Classification Search ................ 536/24.1, 536/23.1
See application file for complete search history.

(56) References Cited

OTHER PUBLICATIONS

Zakhartchenko, VA et al., Sep. 2001, Quantitation of retroviral-mediated transfer using luciferase in living and lysed cells, BioTechniques, 31:676-684.*
Terouanne, B et al., 2000, A stable prostatic bioluminescent cell line to investigate androgen and antiandrogen effects, Molecular and Cellular Endocrinology, 160:39-49.*
Levine. F et al., 1991, Efficient gene expression in mammalian cells from dicistronic transcriptional unit in an improved retroviral vector, Gene, 108:167-174.*
Yee, J-K et al., 1987, Gene expression from transcriptionally disabled retroviral vectors, PNAS, 84:5197-5201.*
Hwang, J-J et al., 1997, A conditional self-inactivating retrovirus that uses a tetracycline-responsive expression system, Journal of Virology, 71:7128-7131.*
Hu, W-S and Pathal, VK., 2000, Design of retroviral vectors and helper cells for gene therapy, Pharmacol. Reviews, 52:493-511.*
Genes V, Oxford University Press, Ed. Lewin, 1994, pp. 847-849.*
GenBank Accession No. NM_007942. Oct. 4, 2003.
GenBank Accession No. E00630. Sep. 29, 1997.
GenBank Accession No. X02158. Jun. 22, 1993.
GenBank Accession No. U94788. Jul 17, 2001.
GenBank Accession No. M11921. Nov. 8, 1994.
GenBank Accession No. M11922. Nov. 8, 1994.
GenBank Accession No. D10493. May 29, 2002.
GenBank Accession No. AAA58637. Dec. 31, 1994.
GenBank Accession No. AH002962. Jan. 8, 1995.
GenBank Accession No. U29874. Feb. 29, 1996.
GenBank Accession No. U44839. Apr. 25, 1996.
GenBank Accession No. P04628. Sep. 15, 2003.
GenBank Accession No. X59397. Nov. 6, 2001.
Armstrong et al. 2003. Cancer Cell 3:173-183.
Wilson et al. *Toxicological Sciences*, 66:69-81 (2002).
International Search Report for PCT/US03/23152, mailed Mar. 1, 2005.

* cited by examiner

*Primary Examiner*—Valarie Bertoglio
(74) *Attorney, Agent, or Firm*—Mintz, Levin, Cohn, Ferris, Glovsky and Popeo, P.C.; Ivor R. Elrifi; Cynthia Kozakiewicz

(57) ABSTRACT

The invention relates to compositions containing a polynucleotide encoding for a reporter gene, a selectable marker and a regulatory element, that provide a method for imaging cells in vivo.

7 Claims, 27 Drawing Sheets

Day 5

Day 21

Validation of FLT3 as a Target in MLL Utilizing shRNA and *In Vivo* Imaging

ADW Effects in an Orthotopic Model of Multiple Myeloma

COMPOSITION AND METHOD FOR IMAGING CELLS

RELATED APPLICATIONS

This application claims priority to U.S. Ser. No. 60/398,583, filed Jul. 25, 2002, which is incorporated herein by reference in its entirety.

STATEMENT OF GOVERNMENT SUPPORT

This invention was made with U.S. Government support under National Institutes of Health/National Cancer Institutes grant CA92480. The government has certain rights in the invention.

FIELD OF THE INVENTION

The invention relates to compositions containing a polynucleotide encoding for a reporter gene, a selectable marker and a regulatory element, thus providing a method for imaging virtually any cell type and virtually any cell signaling pathway in vivo.

BACKGROUND OF THE INVENTION

The paradigm of modern drug discovery is centered on the development of therapies directed against specific pathological cell types or specific molecular targets, particularly components of cell signaling pathways. Anticancer drug discovery, for example, has turned away from searches for non-specific cytotoxic agents, and instead is focused on finding therapies directed against cancer-specific molecular targets, which are often components of complex cell signaling pathways. With this paradigm shift arises the need for new methods of validating the efficacy of these therapeutics against the cellular and molecular targets for which they were developed, and for model systems capable of dissecting the complex molecular interactions occuring in multifactorial signaling pathways.

SUMMARY OF THE INVENTION

The invention is based in part on the discovery of compositions that provide for facile and highly sensitive methods for real-time imaging of a cell of interest. The cells is a normal cell or a tumor cell. For the latter cell type, tumor growth, engraftment, and/or metastasis is monitored by observing light emitted from the light-generating gene product. This technique is advantageous for diseases whose cell types are not otherwise readily identifiable. For example, blood cancers (e.g., leukemias) and brain tumors can be imaged using the compositions described herein.

In one aspect, the invention provides a composition that includes a polynucleotide encoding a reporter gene (e.g., a light-generating moiety), a polynucleotide encoding a selectable marker (e.g., a gene product conferring resistance to an antibiotic) and, optionally, a cis-acting regulatory element (e.g., a promoter). Preferably, the selectable marker allows for selection of the polynucleotide in a eukaryotic host.

Any suitable cis-acting regulatory sequence can be used. A "cis-acting regulatory sequence," as used herein, includes a nucleic acid (e.g., DNA) sequence that modulates the expression of one or more genes, and includes, e.g., promoters, enhancers and silencers, and is generally distinct from a trans-acting factor, such as a DNA-binding polypeptide. A suitable promoter for directing expression in endothelial cell, particularly a rodent endothelial cell, is a nucleotide sequence that includes a cis-acting endothelial cell specific regulatory sequence derived from the Ang-2 gene. The Ang-2 regulatory sequence is provided operably linked to a sequence encoding a stable RNA (such as a ribozyme or interfering RNA). Alternatively, the Ang-2 regulatory sequence is provided operably linked to a polypeptide coding sequence. The polypeptide sequence can be an Ang-2 sequence (e.g., the nucleic acid sequence encoding the Ang-2 polypeptide) or a non-Ang-2 sequence (e.g., a nucleotide sequence encoding a polypeptide other than Ang-2, e.g., a bioluminescent gene product). The cis-acting regulatory sequence is preferably provided as an isolated DNA molecule.

Preferably, the enhancer sequence includes a sequence which hybridizes under high stringency conditions to at least 20 contiguous nucleotides of SEQ ID NO:1, or the complement thereof. In various embodiments, the DNA sequence contains less than 1000 nucleotides, 900 nucleotides, 800 nucleotides, 500 nucleotides, 250 nucleotides, 125 nucleotides, 100 nucleotides, 50 nucleotides, or 25 nucleotides of SEQ ID NO:1 while retaining the ability to effect transcription of operably linked sequences in endothelial cells. If desired, the enhancer sequence includes a plurality of copies of a nucleotide sequence comprising a fragment of SEQ ID NO:1 having cis-acting regulatory activity. In embodiments of the invention, the enhancer sequence includes a two, three, four, five, six, ten, fifteen or more copies of a nucleotide sequence comprising a fragment of SEQ ID NO:1 having cis-acting regulatory activity Also provided by the invention is a vector comprising a cis-acting endothelial cell specific enhancer sequence operably linked to a polypeptide coding sequence, or a sequence encoding a stable RNA, as well as a cell including the vector.

The invention further includes a method of directing endothelial-specific expression of a polypeptide, comprising introducing into an endothelial cell a vector containing an Ang-2 derived cis acting regulatory sequence operably linked to sequence encoding the polypeptide. If desired, the polypeptide can be recovered from the endothelial cell.

In one embodiment, the light-generating gene product is a bioluminescent gene product, such as luciferase, and the selectable marker is a neomycin phosphotransferase. If desired, a regulatory element effects inducible expression of the bioluminescent gene product in a cell.

Also within the invention is a vector that includes a polynucleotide encoding a reporter gene (e.g., a light-generating moiety) and a polynucleotide encoding a selectable marker (e.g., a gene product conferring resistance to an antibiotic). Suitable vectors include viral vectors, such as retroviruses.

The invention also includes a polynucleotide encoding a reporter gene (e.g., a light-generating moiety), a polynucleotide encoding a selectable marker (e.g., a gene product conferring resistance to an antibiotic), as well as a vector including a polynucleotide encoding a reporter gene (e.g., a light-generating moiety) and a polynucleotide encoding a selectable marker (e.g., a gene product conferring resistance to an antibiotic).

The cells of the invention are prokaryotic or eukaryotic. Exemplary cells include primary cells, cells from established cells lines, or tumor cells. In some embodiments, the cells are stably transformed, transfected of infected with the polynucleotide or vector of the invention. In one embodiment, the vector is integrated into an endogenous chromosome of the cell.

In other embodiments, the cells are transiently transformed, transfected of infected.

The cells may be additionally provided in animals, i.e., in transgenic non-human animals that include mammals (e.g., non-human mammals). The non-human mammal may be a primate, a rodent (including a rat or mouse), or a horse, cow, dog, cat, pig, goat, sheep, or rabbit.

The invention also includes transgenic non-human animals that include a recombinant nucleic acid molecule stably integrated into the genome of the animal, the molecule including a cis-acting regulatory sequence and a nucleic acid encoding a light-generating gene product. In embodiments of the invention, the regulatory sequence includes, e.g., Ang-2, Flk1, FLT3, AP-2, Her-2/Neu and c-myc. The light-generating gene product includes ferredoxin IV, green fluorescent protein, red fluorescent protein, yellow fluorescent protein, blue fluorescent protein, the luciferase family and the aequorin family. In embodiments of the invention, the recombinant nucleic acid molecule is of human or murine origin.

The invention further provides an isolated cell from the transgenic non-human animal, e.g., a stem cell, a germ cell, a precursor cell or a progenitor cell.

In another aspect, the invention provides a transgenic non-human animal (e.g., a mouse) including a recombinant nucleic acid molecule stably integrated into the genome of the animal, the recombinant nucleic acid molecule including SEQ ID NO:1 and a nucleic acid encoding a light-generating gene product.

In a further aspect, the invention provides a method for the production of a transgenic non-human animal, by introducing a recombinant nucleic acid molecule including a cis-acting regulatory sequence and a nucleic acid encoding a light-generating gene product into a germ cell, an embryonic cell, an egg cell or a cell derived therefrom.

The invention also provides for a method for the identification of a compound capable of modulating angiogenesis, the method including (i) contacting a transgenic non-human animal including a recombinant nucleic acid molecule including SEQ ID NO:1 and a nucleic acid encoding a light-generating gene product stably integrated into the genome of the animal, or a cell thereof, with a test compound; and (ii) measuring the effect of the test compound on the expression of the nucleic acid encoding a light-generating gene product; thereby identifying a compound that modulates angiogenesis. Modulation of angiogenesis increases angiogenesis. Alternatively, modulation of angiogenesis decreases angiogenesis.

The invention also includes a method for imaging a cell containing a polynucleotide of the invention. The method includes contacting a cell with a substrate for the light-generating gene product and detecting light, thereby imaging the cell.

Any cell disclosed herein can be used in the method. For example, the cell can be a normal (i.e., non-tumorous) cell or a tumor cell. Exemplary tumor cells include hematologic tumors. The tumor may be a metastatic tumor, including breast, liver and brain tumor. In various embodiments, the cell is provided in vitro or in vivo.

The invention also provides methods for identifying a tumor inhibitor by providing a non-human mammal that includes a cell carrying a polynucleotide encoding a reporter gene (e.g., a light-generating moiety), a polynucleotide encoding a selectable marker (e.g., a gene product conferring resistance to an antibiotic) and, optionally, a regulatory element (e.g., a promoter). A test agent is administered to the non-human mammal, and the cell is contacted with a substrate for the light-generating gene product. Light emitted from the cell is detected, and the level of emitted light is compared to the level of light emitted in the absence of the test agent. A lower level of emitted light indicates the test compound is a tumor inhibitor.

In another aspect, the invention includes a method for identifying a modulator of a signal transduction pathway. The method includes (i) providing a non-human mammal comprising a cell carrying a transgenic polynucleotide and a regulatory element whose activity is dependent on a component of the signal transduction pathway, (ii) administering a test agent to the non-human mammal, (iii) contacting the cell with a substrate for the light-generating gene product, (iv) detecting light emitted from the cell, and (v) comparing the level of emitted light to the level of light emitted in the absence of the test agent, wherein a lower level of emitted light indicates the test compound is a modulator of the signal transduction pathway.

In another aspect, the invention includes a method of validating the presence or activity of a biological component in a signal transduction pathway, e.g., a tumor-associated signaling pathway. A biological component includes any compound derived from a biological source, and includes nucleic acids such as DNA and RNA, polypeptides, lipids, carbohydrates, hormones, metabolites, organic molecules, and signaling molecules (e.g., cAMP, ADP and ATP). The validation includes the determination that the expression or an activity of a polypeptide or a nucleic acid affects one or more components of a signal transduction pathway. The method includes (i) providing a non-human mammal comprising a cell carrying a transgenic polynucleotide and a regulatory element whose activity is dependent on a component of the signal transduction pathway (e.g., a cis-acting regulatory sequence associated with the signal transduction pathway and a nucleic acid encoding a light-generating gene product; (ii) contacting the non-human mammal with an inhibitor, e.g., iRNA, that decreases or eliminates the presence or activity of the biological component; and comparing the level of emitted light to the level of light emitted in the absence of the inhibitory agent, wherein a lower level of emitted light indicates that the biological component is in the signal transduction pathway.

Also provided by the invention is a cell or cell line that has been infected with a retrovirus. A preferred cell line is MDA-MB231 cells infected with retrovirus encoding a fusion of luciferase and neomyocin phosphotransferase (pMMP-Luc-Neo). Other preferred cell lines infected with pMMP-LucNeo retrovirus are indicated in Table 2.

Also within the invention is a transgenic animal administered a composition containing luciferase expressed from the Ang-2 promoter.

In a further aspect, the invention includes a method for detecting cells. In one aspect the cell is a non-tumorogenic cell. In yet another aspect the cell is a tumor cell. Preferred tumor cells include hematologic tumor cells and breast tumor cells. Preferred cells include MDA-MB231, U87, K562, 32D/p210, RS(4;11), TS(4;11), Ba/F3-Flt3, NB4, and cells listed in Table 2.

In another aspect the invention includes a method for detecting the progression of metastatic cancers.

The invention additionally provides a method for identifying both engrafted and proliferating cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present Specification, including definitions, will control. In addition, the materials, methods, and examples are illustrative only and not intended to be limiting.

Other features and advantages of the invention will be apparent from the following detailed description and claims.

DETAILED DESCRIPTION OF THE INVENTION

Figure 1:
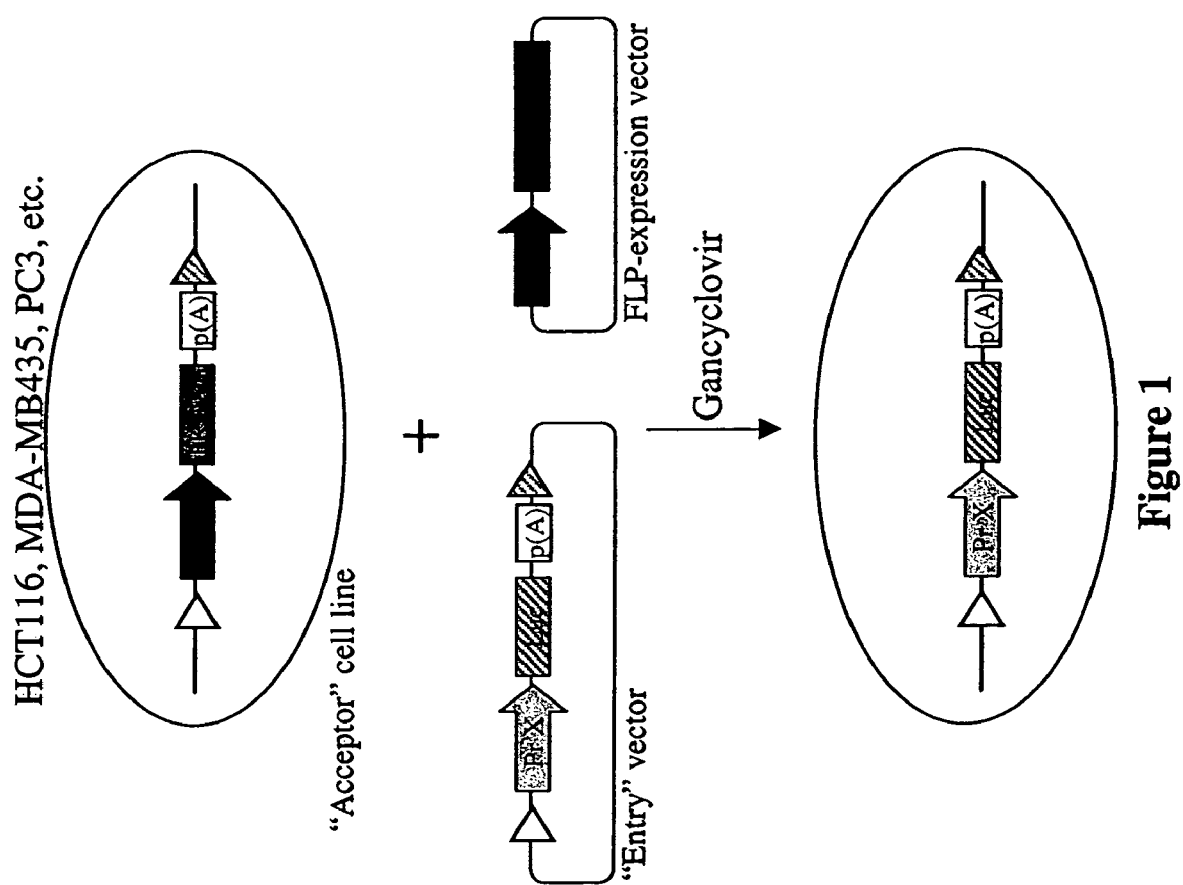
FIG. 1 is a schematic representation of the creation of reporter cells utilizing FLP-mediated recombination of an "entry" vector into a master "acceptor" cell line.

This invention provides compositions that include a polynucleotide encoding a reporter gene (e.g., a light-generating moiety), a polynucleotide encoding a selectable marker (e.g., an antibiotic) and a regulatory element (e.g., a promoter), and methods for imaging cells using these polynucleotides.

In general, any light-generating moiety that gives off light can be used as the reporter gene. In some embodiments, the light-generating moieties are bioluminescent proteins, such as firefly [Photinus pyralis] luciferase, obelin and aequorin. Preferred light-generating moieties include firefly luciferase, which has been used for quantitative determination of specific substances in biology and medicine for many years.

In general, any gene encoding a gene product that allows for selection of the cell carrying the polynucleotide can be used as the selectable marker. Such selection systems are well known in the art. Examples of selectable markers include, but are not limited to, known genes encoding resistance to antibiotics such as the aminoglycoside antibiotics (including, e.g, neomycin, hygromycin, kanamycin, bleomycin, G418. A suitable marker for use in aminoglycoside based selection is the neomycin phosphotransferase (neo) gene (see, e.g., Potrykus et al., Mol. Gen. Genet. 199:183-188 (1985). Other selectable markers include the dihydrofolate reductase (DHFR) gene, which confers resistance to methotrexate (Thillet et al., J. Biol. Chem. 263:12500-12508 (1988). Fluorescent proteins are selected by, for example, fluorescence-activated cell sorting.

The polynucleotide optionally contains a regulatory element. By "regulatory element" is meant a minimal DNA sequence sufficient to direct transcription. Regulatory elements are constitutive or inducible, and may be coupled to additional sequences or "elements" which render promoter-dependent gene expression cell-type specific, tissue-specific or inducible by external signals or agents; such elements may be located in the 5' or 3' region of the native gene, or within an intron. Promoters are exemplary regulatory elements. By "heterologous promoter" is meant a promoter other than a naturally occurring promoter directing transcription of a reporter gene or selectable marker.

The promoter is preferably operably linked to the reporter gene and/or selectable marker. By "operably linked" is meant that a coding sequence and a regulatory sequence(s) are connected in such a way as to permit gene expression when the appropriate molecules (e.g., transcriptional activator proteins) are bound to the regulatory sequence(s).

Suitable constitutive promoters include, e.g., SV40, CMV, CDK9, PGK, and ubiquitin C. Preferred promoters include ubiquitin C, PGK and CMV. For embodiment in which the use of a lineage-specific promoter is desirable, any well-known organ/tissue-specific promoter can be used. These various regulatory elements are capable of affecting various tissues. In some embodiments, the regulatory element has an effect on proliferating endothelial cells. Preferred regulatory elements include Ang2, Flk1, and VEGFR2. In some embodiments, the regulatory element is active in breast tissue. Preferred regulatory elements can include AP-2, Her-2/Neu and c-Myc. Suitable regulatory promoters for various tissue, or tumors derived from such tissues, are listed in Table 1:

TABLE 1

| Promoter | Tissue/Tumor |
|---|---|
| Calcineurin A-alpha | Brain |
| Synapsin-I | Brain |
| Glial fibrillary acidic protein | Brain |
| Nerve growth factor receptor | Brain |
| Prostate-specific antigen | Prostate |
| Kallikrein | Prostate |
| Androgen receptor | Prostate |
| Tyrosinase | Melanocytes |
| Micro-opthalmia | Melanocytes |
| Gata-4, -5, -6 | Heart |
| Atrial natriuretic protein | Heart |
| Cardiac myosin heavy chain | Heart |
| Troponin | Heart |
| d-Hand | Heart |
| Alpha1-antitrypsin protease | Liver |
| CEA | Liver |
| Alpha-fetoprotein | Liver |
| Amylase | Pancreas |
| CEA | Pancreas |
| c-erbB2 | Pancreas |
| CEA | Lung |
| Surfactant A and B | Lung |
| Gastrin releasing peptide | Lung |
| AVP | Lung |
| AP-2 | Breast |
| Alpha- and Beta-lactalbumin | Breast |
| Her-2/Neu | Breast |
| c-Myc | Breast |
| Osteocalcin | Bone |
| CEA | Colon |
| Cyclooxygenase-2 | Colon |
| Myosin | Muscle |
| Vav | Hematologic |
| CD33, CD34, etc. | Hematologic |
| Gata-1 | Hematologic |
| Immunoglobulin, CD3, CD10, CD19, etc. | Lymphocytes |
| VEGF family | Angiogenesis |
| VEGFR-1 (Flt-1) | Angiogenesis |
| VEGFR-2 (Flk-1, KDR) | Angiogenesis |
| VEGFR-3 (Flt-4) | Angiogenesis |
| Ang1, 2, 3, and 4 | Angiogenesis |
| Tie1 and 2 | Angiogenesis |
| Ephrin-B1, -B2, and -A1 | Angiogenesis |
| EphA2, B2, B3, and B4 | Angiogenesis |
| Erythropoietin | Kidney |
| Renin | Kidney |
| CEA | Ovary |

An example of a promoter that can be used in the polynucleotides described herein is a cis-acting regulatory sequence derived from the genomic region 5' to the start of transcription of the murine Ang-2 gene. A 1220 nucleotide murine Ang-2 sequence containing cis-acting activity is shown below:

(SEQ ID NO:1)
GAGTCTTCCCAGTACCGATCTCTGCAGCATTAACTTCTAGTCATGAAGGGGTGGTGACTCTGGACCAGCAGAGCCACA

GAGCTGGAAGTGTTTTAGAAGTCAGTGCAGCCCCCAGCTTTTATGGCCAGGGGCTTTTGAACTTAATTAAAAGGGGAA

AGTGATTTGCCTGAGCCCACTGACTGGGACTAATTTAATCAGGAACATGCCACAGAGTGATGAGCCCGAGGAAACCCT

-continued

```
GATACAGTGAAGGAAAAGGTGTATGTTTGTTTCCTCTCGACATACTTCACTCAAATATCTATTGTTACTTAACAGACA

ATTAATCAGGCCAAACCACTTTAAGTTTTATTTGTATAGTATTTTGTGTTAAGGCACAGACATGTGAGTGCTGAGAAA

ACTGATGTTGGTAACTTGATTTAATAATATCAAACTGGGTTAAAATAAAAAAAAATGTGCATAACTTAAAAAAAAAAC

CAAATACCAACAAGACTTTACTTCCCCTTGGAAAAGCACATTTACAAGGGCTGATCTTAGCCTTTATATTTACAATAA

AGAAAATAAACCAAGGTCCCGATATAGCTGTAATTTTATTCCTAAAAGAACAGAAACTTTCACTATGCTTTAAAATTA

AAGTGATTACCTCAGATACTCTGCAAGCTTAGCCTACAAACGAGCAGACAGACAACAGAGCCCCAGCTACTCTCTAGG

AAATAATTAGGGTGGTGCCTCTGACATGCCCAGGGGTCTTGTGGCTGGTCTGTGTTCCCAGAAGGCTTCTGCAGTACA

CAGTCCTTTGGGGCAGTAAGCACTATGCTCTGATTTTTCCTGTTGCCTGGCTAGTGACCCCCTACAGGAAGATAGTGG

GTGAGCCAGGGGGCGGAGCGGCTGGCTGCACATGTCTGGCTGCTCTTATCAACTTATCATATAAGGGAAGGAAAGTGA

TTGATTCGGATACTGACACTGTAGACTCAGGGGAGAAACAAAGAGTCCGTGCAGACCTCTGGAGTGAGCAGGGCTGCT

CCTTCCTCTCAGGACAGCTCCGAGTGTGCCGGGGAGAAGAGAAGAGAAGAGACAGGCACTGGGAAAGAGCCTGCTGCG

GGACGGAGAAGGCTCTCACTGATGGACTTATTCACACGGCACAGCCCTGTGCCTTAGACAGCAGCTGAGAGCTCAGGA

CGCAAGTTTGCTGAACTCACAGTTTAGAACCCAAAAAGAGAGAGAATG
```

In the sequence shown, transcription begins at nucleotide 1008, while translation at the site encoded by nucleotides 1218-1220 (the final ATG shown).

The Ang-2 cis-acting regulatory sequence is preferably provided as an isolated polynucleotide sequence, e.g., an isolated DNA sequence. By "isolated DNA" is meant DNA that is free of the genes which, in the naturally-occurring genome of the organism from which the DNA of the invention is derived, flank the Ang-2 gene. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

The Ang-2 cis-acting regulatory elements may be contiguous or separated by DNA not involved in the regulation of transcription, e.g., an enhancer element may be in a position immediately adjacent to the promoter element or up to several kilobases upstream or downstream of the transcriptional start site. The cis-acting DNA is preferably derived from the 5' region of a mammalian Ang-2 gene, such as that of the mouse (SEQ ID NO:1), and regulates preferential expression in endothelial muscle cells of a polypeptide-encoding DNA to which it is operably linked. The Ang-2 cis-acting regulatory sequence can include any portion of SEQ ID NO:1, so long as the portion effects endothelial cell-specific gene expression. Thus, in some embodiments, the cis-acting regulatory sequence is less than, e.g., 1000 nucleotides, 750 nucleotides, 500, nucleotides 250 nucleotides, 125 nucleotides, 100 nucleotides, 50 nucleotides, or less than 25 nucleotides in length. If desired, multiple copies (e.g., 2, 3, 5, 10, or 15 copies) of an Ang-2 cis-acting regulatory sequence can be provided operably linked to a sequence encoding a gene product (e.g., a sequence encoding a stable RNA or a polypeptide coding sequence).

The Ang-2 enhancer including SEQ ID NO:1, or a portion thereof, may be immediately contiguous to a polypeptide-encoding DNA. Alternatively, the cis-acting sequence may be separated by 5, 10, 20, 30, 40, 50, 75, or 100 nucleotides from the polypeptide-encoding DNA. In addition to or alternatively, the enhancer may be contiguous to, or be separated by 5, 10, 20, 30, 40, 50, 75, or 100 nucleotides from a heterologous promoter.

Preferably, expression of a polypeptide under the control of the Ang-2-sequence is at least 50% greater (e.g., as measured in the amount of polypeptide-encoding mRNA transcript), preferably at least 100% greater, more preferably at least 200% greater, and still more preferably at least 400% greater in endothelial muscle cells than in non-endothelial cells. Most preferably, the Ang-2 derived sequence directs endothelial cell-specific polypeptide expression and directs negligible polypeptide expression in non-endothelial cell types. The enhancer sequence may in addition regulate developmental stage-specific expression, e.g., preferential expression in embryonic cells, of a polypeptide-encoding sequence.

Sequences responsible for conferring smooth muscle cell-specificity in the 5' Ang-2 region can be localized more precisely within the 5' region using methods well-known in the art, e.g., by constructing plasmids containing successively smaller portions of the sequence shown above (SEQ ID NO:1) placed upstream of a luciferase reporter gene (or any of the many reporter genes known in the art) in an assay analogous to that shown in Example 8, and determining if the portion of the upstream sequence directs expression of the reporter gene. Increased expression of the reporter gene in endothelial cells compared to other cell types (i.e., non-endothelial cell types) indicates that the region of the Ang-2 5' sequence directs endothelial-cell specific gene expression.

The cis-acting Ang-2 regulatory sequence may be operably linked to a DNA sequence encoding a polypeptide that is not Ang-2 (i.e., a heterologous polypeptide), and function to regulate endothelial cell-specific transcription of the polypeptide-encoding sequence.

The invention also provides a method of directing endothelial cell-specific expression of a protein by introducing into an endothelial cell a DNA containing a sequence encoding the protein operably linked to an Ang-2 promoter.

The polynucleotide is preferably provided in a vector, which can a plasmid, cosmid, yeast artificial chromosome, bacterial artificial chromosome, or viral vector. The terms "construct" or "vector" refers to any plasmid or virus. In some embodiments, the vector sequences include or are derived from retroviral sequences, e.g., lentivirus. Preferred retrovirus constructs include pMMP, pMSCV and VSV-G pseudotyped retrovirus.

Cells

Both prokaryotic and eukaryotic cells are useful in the invention. In some embodiments, the cell is a eukaryotic cell. Appropriate constructs or vectors, containing desired regulatory elements are prepared. These vectors are used to generate constructs capable of expressing desired light-generating proteins in a variety of eukaryotic cells. Preferred eukaryotic cells include primary cells, embryonic stem cells and cell lines.

The invention describes methods of creating stimuli-responsive reporter cell lines. With such master "acceptor" cell lines, co-isogenic reporters of any pathway of interest are generated by, e.g., FLP-mediated recombination and selection. "Acceptor" cell lines are eukaryotic cell lines modified to accept nucleic acid vectors by recombination, such as FLP or Cre-Lox.

Examplary eukaryotic cells modified to constitutively express LucNeo are listed in Table 2. The cells are also useful to be modified as described to be "acceptor cells." Introduction of the LucNeo polynucleotide vector is performed by any means described above, or known by those of skill in the art. Expression of luciferase is in a stimuli-responsive manner. Alternatively, expression of luciferase is constituitive.

TABLE 2

Generation of tumor cell LucNeo cell lines

| Model | Cell line |
| --- | --- |
| Breast Cancer | MDA-MD231 |
|  | 4T1 |
|  | MDA-MB435 |
|  | MDA-MB468 |
|  | ENDA-A |
| Prostate cancer | PC-3 |
|  | LNCap |
| Brain tumors | U87 |
|  | U118 |
|  | U251 |
|  | LN308 |
|  | LN428 |
|  | LN827 |
|  | Daoy |
|  | C6 |
| Ovarian cancer | SKOV3 |
| Colon cancer | HCT116 |
|  | ProB |
| Sarcomas | EWS |
|  | A673 |
| Lung cancer | NCI H520 |
| Melanoma | B16-F10 |
|  | MTLN3 |
|  | A375 |
| Leukemia | 32D-p210 |
|  | TS(4;11) |
|  | RS(4;11) |
|  | K562 |
|  | Ku812F |
|  | HL60 |
|  | MEG01 |
|  | MOLM13 |
|  | Ba/F3-FLT |
|  | Multiple Ba/F3 FLT3 and BCR/ABL |
| Multiple myeloma | MM1S |
|  | MM1R |
|  | RPMI8226 |

TABLE 2-continued

Generation of tumor cell LucNeo cell lines

| Model | Cell line |
| --- | --- |
| Metastases | Lewis Lung Ca |
|  | MDA-MB435-Lung |
|  | MDA-MB231-MET |
| Liver cancer | HepG2 |

Transgenic Animals

The invention additionally provides transgenic animals carrying polynucleotides with a first nucleic acid encoding a light-generating gene product and a second nucleic acid encoding a selectable marker.

Methods for constructing transgenic animals are known in the art. Preferred transgenic animals include rodents (e.g., mice and rats). The preparation of a transgenic mammal requires introducing a nucleic acid construct that will be used to express a nucleic acid encoding a light-generating fusion protein into an undifferentiated cell type, e.g., an embryonic stem (ES) cell. The ES cell is then injected into a mammalian embryo, where it will integrate into the developing embryo. The embryo is then implanted into a foster mother for the duration of gestation.

Embryonic stem cells are typically selected for their ability to integrate into and become part of the germ line of a developing embryo so as to create germ line transmission of the heterologous gene construct. Thus, any ES cell line that has this capability is suitable for use herein. One mouse strain that is typically used for production of ES cells is the 129J strain. A preferred ES cell line is murine cell line D3 (American Type Culture Collection catalog no. CRL 1934). The cells are cultured and prepared for DNA insertion using methods well known in the art, such as those set forth by Robertson (Robertson, In: *Teratocarcinomas and Embryonic Stem Cells: A Practical Approach*, E. J. Robertson, ed., IRL Press, Washington, D.C., 1987.). Insertion of the nucleic acid construct into the ES cells can be accomplished using a variety of methods well known in the art including for example, lentiviral infection, electroporation, microinjection, and calcium phosphate treatment.

Light emission from pigmented animals is significantly attenuated (>10 fold). However, the most commonly utilized and best defined mouse genetic models are in a C57BL/6 (B6) background, and B6 mice are pigmented. To facilitate creation of mouse genetic models for imaging, ES cells have been generated from albino B6 mice (C57BL/6-Tyr$^{c/c}$). These ES cells, named Tyr-ES1 and Tyr-ES2, are used to create C57BL/6 co-isogenic mouse models for in vivo imaging.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of an heterologous nucleic acid, such as DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g., rats, mice, etc. Preferably, the transgenic animals are mice.

Transgenic animals comprise an heterologous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The heterologous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g., transcriptional activator proteins, are bound to the regulatory sequence(s). The transgenic animals of the invention can comprise other genetic alterations in addition to the presence of the heterologous gene. For example, the host's genome may be altered to affect the function of endogenous genes (e.g., endogenous Ang genes), contain marker genes, or other genetic alterations such as are described in the Examples.

Examples of selectable markers include positive selectable markers and negative selectable markers. Positive selectable markers include drug resistance genes; e.g., neomycin resistance genes or hygromycin resistance genes, or beta-galactosidase genes. Negative selectable markers, e.g., thymidine kinase gene, diphtheria toxin gene and ganciclovir are useful in the heterologous gene construct in order to eliminate embryonic stem (ES) cells that do not undergo homologous recombination. The selectable marker gene is usually operably linked to its own promoter or to another strong promoter from any source that will be active or can easily be activated in the cell into which it is inserted; however, the marker gene need not have its own promoter attached as it may be transcribed using the promoter of the light-generating fusion protein gene to be suppressed. In addition, the marker gene will normally have a polyA sequence attached to the 3' end of the gene; this sequence serves to terminate transcription of the gene.

Transgenic animals can be crossed to other disease model systems to allow real time visualization of pathological changes as they evolve. General tumor-specific reporters can be used to follow development of tumors in real time (e.g., E2F1-Luc or hypoxia-responsive-Luc in mouse models of cancer). Signal transduction pathway specific reporters can be used to follow pathological activation of that pathway in various disease models (e.g., a WNT-reporter in a APC/min background to monitor development of colonic polyps and tumors, a estrogen-reporter in breast cancer models, a NF-KB reporter in a mouse model of arthritis).

Transgenic mice with cell lineage-restricted regulatory elements can be used to follow proliferation of various cell types (e.g., growth cone specific regulatory elements to follow neural regeneration). Lineage restricted luciferase expressing mice can be used as donors for experiments studying trans-differentiation (e.g., transplanting hematopoietic stem cells from a mouse with neuron-restricted luciferase expression to follow trans-differentiation from hematopoietic to neuronal cells).

In another aspect, transgenic mice are created in which luciferase is constitutively expressed in all cells. Cells isolated from such mice can be used as "donor" cells for various transplantation experiments (e.g., bone marrow transplantation with or without retroviral transduction with transforming oncogenes).

Exemplary reporter cell lines generated by the methods of the invention are shown in Table 3. Suitable sources for nucleic acids useful in generating these cell lines can be found at, e.g., GenBank Accession Numbers NM_007942; E00630; X02158; U94788; M11921; M11922; D10493; AAA58637 and AH002962.

TABLE 3

| Reporter cell lines | HepG2 EpoLuc |
| --- | --- |
|  | HepG2 CMV-Luc |
|  | RAS/RAF reporter cell lines |
|  | WNT-reporter |
|  | AKT-reporter |
|  | p53-reporter |
|  | caspase-reporter |
|  | ETS-reporter |

Exemplary transgenic animals generated by the methods of the invention are shown in Table 4. Suitable sources for nucleic acids useful in generating these transgenic mice can be found at, e.g., GenBank Accession Numbers U29874; U44839; $P_{04628}$ and X59397.

TABLE 4

| Reporter Transgenic mice | Ubiquitin C |
| --- | --- |
|  | Ang2 |
|  | VEGFR2 |
|  | WNT-responsive |
|  | Hypoxia-responsive |

Methods of Imaging Cells

The present invention includes any light-generating gene product that is detectable. Light-generating gene products include ferredoxin IV, green fluorescent protein, red fluorescent protein, yellow fluorescent protein, blue fluorescent protein, the luciferase family and the aequorin family. A cell containing a polynucleotide of the invention may be imaged as long as a suitable substrate for the light-generating gene product is available, if a substrate is required for the light-generating gene product to function. Substrates of the light-generating gene product can be endogenous to the cell or applied to the cell or system. A substrate is selected that is suitable for the light-generating product used. For example, when luciferase is used as the light generating product, suitable substrates include luciferin and coelenterazine.

Members of the luciferase family have been identified in a variety of prokaryotic and eukaryotic organisms. Luciferase and other enzymes involved in the prokaryotic luminescent (lux) systems, as well as the corresponding lux genes, have been isolated from marine bacteria in the *Vibrio* and *Photobacterium* genera and from terrestrial bacteria in the *Xenorhabdus* genus, also called photorhalodus. An exemplary eukaryotic organism containing a luciferase system (luc) is the North American firefly *Photinus pyralis*. Firefly luciferase has been extensively studied, and is widely used in ATP assays. cDNAs encoding luciferases from *Pyrophorus*

*plagiophthalamus*, another species, click beetle, have been cloned and expressed (See, Wood et al., 1989, *Science* 244: 700-702). This beetle is unusual in that different members of the species emit bioluminescence of different colors. Four classes of clones, having 95-99% similarity with each other, were isolated. They emit light at 546 nm (green), 560 nm (yellow-green), 578 nm (yellow) and 593 nm (orange).

Luciferases requires a source of energy, such as ATP, NAD(P)H, and the like, and a substrate, such as luciferin, decanal (bacterial enzymes) or coelentrizine and oxygen. The substrate luciferin must be supplied to the luciferase enzyme in order for it to luminesce. Thus, a convenient method for providing luciferin is to express not only the luciferase but also the biosynthetic enzymes for the synthesis of the substrate decanal. Oxygen is then the only extrinsic requirement for bioluminescence, in bacteria expressing these proteins from the Lux operon.

The emitted light produced from the reaction can be conveniently detected using non-invasive imaging technology. Imaging of light-generating moieties is performed using methods known in the art. A suitable method for quantifying the in vivo effect is Xenogen IVIS™ technology. For example, imaging can be performed using a photodetector capable of detecting extremely low levels of light and integrating photon emission until an image is constructed. Examples of such sensitive photodetectors include devices that intensify the single photon events before the events are detected by a camera, and cameras (cooled, for example, with liquid nitrogen) that are capable of detecting single photons over the background noise inherent in a detection system.

Once a photon emission image is generated, it is typically superimposed on a "normal" reflected light image of the subject to provide a frame of reference for the source of the emitted photons (i.e., localize the light-generating moiety conjugates with respect to the subject). Such a "composite" image is then analyzed to determine the location and/or amount of a target in the subject.

The non-invasive imaging technology can be useful in a variety of applications in the present invention. The vector constructs, cells and transgenic animals described herein contain a sequence encoding a detectable gene product, e.g., a luciferase gene, operably linked to a transcription regulatory element, e.g., a promoter. The promoter may be from the same species as the transgenic animal or from a different species. The promoter can be derived from any gene of interest (see Table 1). In one embodiment of the present invention, the promoter is derived from a gene whose expression is induced during tumor growth, for example breast cancer. Thus, when breast cancer cells develop in a transgenic animal carrying a vector construct of the present invention, the promoter is induced and the animal expresses luciferase, which can then be monitored in vivo using the non-invasive imaging technology described. Other embodiments of the invention allow for imaging of transgenic non-human mammals with luciferase expressed from promoters active in proliferating endothelial cells, e.g., Ang2, thus, angiogenesis and other conditions of pathological vascular proliferation can be imaged. In another embodiment, normal cells, for example hematopoietic cells, that have been stably integrated with luciferase expressed from various stimuli-responsive promoters can be followed in vivo during engraftment and proliferation. In yet another aspect of the invention, the ability to follow the progression of metastatic disease is possible.

Identification of Compounds that Modulate Angiogenesis

The prevention or inhibition of angiogenesis, e.g., tumor-associated angiogenesis, is an important therapeutic goal. Further, methods of stimulating neovascularization (by angiogenesis and/or vasculogenesis) are critical in the treatment of diseases such as heart disease and diabetes. As such, the present invention provides for a method for the identification of compounds capable of modulating angiogenesis, including pro- and anti-angiogenic compounds. Transgenic mice expressing luciferase from the Ang-2 promoter allow endothelial cell-specific localization within vascularized tissues. Angiogenic stimuli, including tumors or cells thereof, or angiogenic factors (e.g., VEGF, bFGF and PDGF) implanted in natural or biosynthetic materials (e.g., Matrigel), are implanted into the mice to induce angiogenesis. Test compounds are introduced to the mice using methods known to those skilled in the art, such as intravenous or subcutaneous injection. The effect of the test compound on luciferase activity is measured in the compound-treated mice, and compared to luciferase activity in control mice. Thus, the impact of the compound on angiogenic pathways involving Ang-2 is determined. Angiogenesis is be measured by methods known in the art, including angiography, endothelial cell proliferation, and measurement of endothelial cell specific markers.

Validation of Biological Components in Cell Signaling Pathways

High-throughput analytical systems such as gene arrays provide large quantities of potential biological components of signal transduction pathways that must be validated. An embodiment of the present invention includes a method wherein potential components of a signaling pathway are identified and then tested using the in vivo model system described herein (See FIG. 17).

Once a biological component predicted to belong to a signal pathway is identified by means known in the art, an inhibitor of the biological component is generated (e.g., an interfereing RNA, anti-sense nucleic acid, or blocking antibody). For example, a retrovirus such as a lentivirus is used to express short hairpin RNA interference molecules targeting the potential component. This inhibitor is then contacted with a non-human mammal or a cell carrying a transgenic polynucleotide including a nucleic acid encoding a light generating gene product and a nucleic acid encoding a regulatory element, such as a promoter, whose activity is dependent upon a component of the signal transduction pathway under study. If the light-generating gene product requires a subtrate, this subtrate is contacted with the mammal or cell. Emitted light is detected from the mammal or cell, and the level of which is compared with the level of emitted light in the absence of the inhibitor. A decrease in the level of emitted light indicates that the biological component is in the signal transduction pathway.

Two methods of creating inhibitors include interfering RNA and antisense nucleic acids.

Interfering RNA

Interfering RNA (iRNA or RNAi) is used in gene silencing by obstructing the translation process in eukaryotic organisms. In one aspect of the invention, gene expression can be attenuated by RNA interference. One approach well-known in the art is short interfering RNA (siRNA) mediated gene silencing where expression products of a gene are targeted by specific double stranded nucleic acid derived siRNA nucleotide sequences that are complementary to at least a 19-25 nt long segment of the targeted gene transcript, including the 5' untranslated (UT) region, the ORF, or the 3' UT region. See, e.g., PCT applications WO00/44895, WO99/32619, WO01/75164, WO01/92513, WO01/29058, WO01/89304, WO02/16620, and WO02/29858, each incorporated by reference herein in their entirety. Targeted genes can be a gene, or an upstream or downstream modulator of the gene, such as, e.g., a transcription factor, a kinase or phosphatase that interacts with a biological component polypeptide, and polypeptides involved in a signal transduction pathway.

In an example, a hairpin RNAi product is a siRNA. The regulatory sequences flanking the biological component sequence may be identical or may be different, such that their expression may be modulated independently, or in a temporal or spatial manner. In a specific embodiment, siRNAs are transcribed intracellularly by cloning the target gene templates into a vector containing, e.g., a RNA pol II transcription unit from the smaller nuclear RNA (snRNA) U6 or the human RNase P RNA H1. One example of a vector system is the GeneSuppressor_RNA Interference kit (commercially available—from Imgenex). The U6 and H1 promoters are members of the type m class of Pol III promoters. The +1 nucleotide of the U6-like promoters is always guanosine, whereas the +1 for H1 promoters is adenosine. The termination signal for these promoters is defined by five consecutive thymidines. The transcript is typically cleaved after the second uridine. Cleavage at this position generates a 3' W overhang in the expressed siiRNA, which is similar to the 3' overhangs of synthetic siRNAs. Any sequence less than 400 nucleotides in length can be transcribed by these promoter, therefore they are ideally suited for the expression of around 21-nucleotide siRNAs in, e.g., an approximately 50-nucleotide RNA stem-loop transcript.

Antisense Nucleic Acids

An "antisense" nucleic acid comprises a nucleotide sequence that is complementary to a "sense" nucleic acid encoding a protein (e.g., complementary to the coding strand of a double-stranded cDNA molecule or complementary to an mRNA sequence). In specific aspects, antisense nucleic acid molecules are provided that comprise a sequence complementary to at least about 10, 25, 50, 100, 250 or 500 nucleotides or an entire gene coding strand, or to only a portion thereof.

In one embodiment, an antisense nucleic acid molecule is antisense to a "coding region" of the coding strand of a nucleotide sequence encoding a protein. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding a protein. The term "noncoding region" refers to 5' and 3' sequences which flank the coding region that are not translated into amino acids (i.e., also referred to as 5' and 3' untranslated regions). An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used). Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically contacted with the mammal or cell or generated in situ such that they hybridize with or bind to cellular mRNA and/or genomic DNA encoding a protein to thereby inhibit expression of the protein (e.g., by inhibiting transcription and/or translation). The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface (e.g., by linking the antisense nucleic acid molecules to peptides or antibodies that bind to cell surface receptors or antigens). The antisense nucleic acid molecules can also be delivered to cells using the vectors described herein. To achieve sufficient nucleic acid molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other. See, e.g., Gaultier, et al., 1987. *Nucl. Acids Res.* 15: 6625-6641. The antisense nucleic acid molecule can also comprise a 2'-o-methylribonucleotide (See, e.g., Inoue, et al. 1987. *Nucl. Acids Res.* 15: 6131-6148) or a chimeric RNA-DNA analogue (See, e.g., Inoue, et al., 1987. *FEBS Lett.* 215: 327-330.

In one embodiment, an antisense nucleic acid of the invention is a ribozyme. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes as described in Haselhoff and Gerlach 1988. *Nature* 334: 585-591) can be used to catalytically cleave NOVX mRNA transcripts to thereby inhibit translation of an mRNA.

In various embodiments, the nucleic acids of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids. See, e.g., Hyrup, et al., 1996. *Bioorg Med Chem* 4: 5-23. As used herein, the terms "peptide nucleic acids" or "PNAs" refer to nucleic acid mimics (e.g., DNA mimics) in which the deoxyribose phosphate backbone is replaced by a pseudopeptide backbone and only the four natural nucleotide bases are retained. The neutral backbone of PNAs has been shown to allow for specific hybridization to DNA and RNA under conditions of low ionic strength. The synthesis of PNA oligomer can be performed using standard solid phase peptide synthesis protocols as described in Hyrup, et al., 1996. supra; Perry-O'Keefe, et al., 1996. *Proc. Natl. Acad. Sci. USA* 93: 14670-14675.

EXAMPLES

The invention will be further illustrated in the following non-limiting examples.

Example 1

Construction of a Cell Line with a Vector Containing Nucleic Acids Encoding Luciferase and Neomycin Phosphotransferase A cell line with a vector containing a luciferase and neomycin phosphotransferase is constructed using FLP-mediated recombination. A schematic representation of the construction scheme is shown in FIG. 1. First, "acceptor" cell lines are generated by introducing a PGK regulatory element driving a TK-neo fusion, single integrated copy of a positive-negative selection cassette, flanked by heterologous FRT sites (FIG. 2). This is accomplished either by transfection of plasmids, or retroviral transduction with an enhancer-deleted retrovirus. The latter approach affords easier control over integrated copy number than the first approach. A series of master acceptor cell lines, utilizing cell lines of greatest utility for in vitro and in vivo testing (e.g., HCT 116, MDA-MB435, PC3, etc.) are created using these techniques.

For each cell line of interest, 10-20 clones are initially tested to find a master "acceptor" clone to be used to generate all subsequent reporters by FLP-mediated recombination. Each set of cell clones is tested for a proper, integrated ectopic DNA sequence ("acceptor" site) whose expression is not significantly effected by genetic elements surrounding the integration site, i.e., not near a strong regulatory element or silencing element. An aliquot of each clone is tested by recombining in a regulatory elementless luciferase allele.

Figure 3:
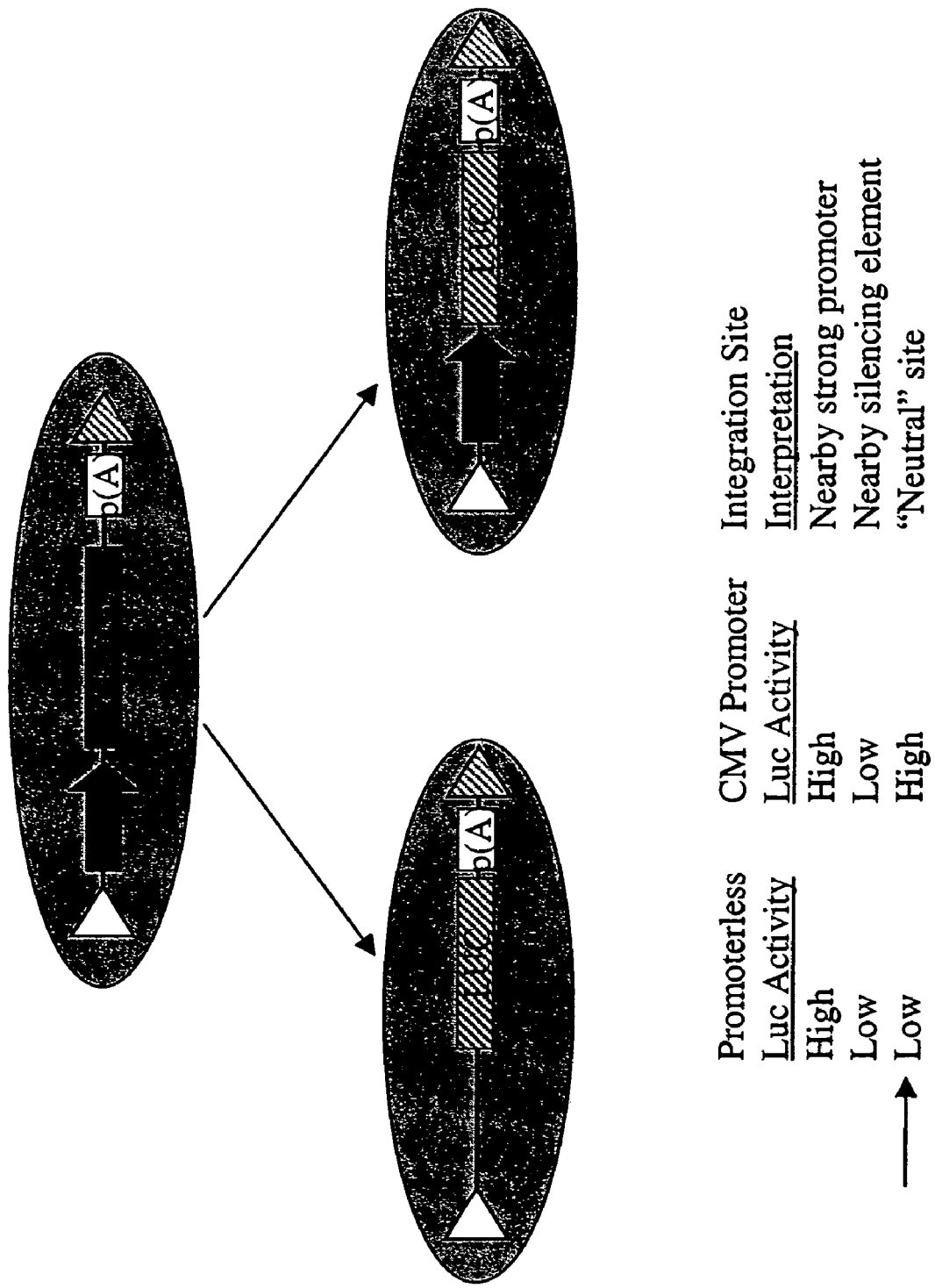
FIG. 3 is a schematic representation showing testing of cell clones by FLP-mediated introduction of a promoterless vs. a CMV-driven luciferase. The relative luciferase activity of resulting recombinants reveals surrounding genetic elements that modify transcription from the integration site. A clone with a "neutral" integration site would be chosen as a master "acceptor" clone for that cell line.

Another aliquot is recombined in an allele of luciferase driven by a CMV or SV40 regulatory element as shown in FIG. 3. The figure shows testing of cell clones by FLP-mediated introduction of a promoterless vs. a CMV-driven luciferase. The relative luciferase activity of resulting recombinants implicates surrounding genetic elements that might potentially modify transcription from the integration site. A clone with a "neutral" integration site is chosen as a master "acceptor" clone for that cell line. Thus, for each original transformant, there are two, co-isogenic derivatives—one containing no added regulatory element adjacent to luciferase and the other a strong constitutive one. Clones demonstrating the greatest difference between the expression of these two constructs—each integrated at the same genomic site—are those in which the FRT-flanked "acceptor" site is embedded in a chromatin region that is neither silenced nor constitutively activated for transcription. For each cell line, a single clone with these characteristics is used for all subsequent generation of derivative reporter subclones by the methods outlined below.

Figure 4A:
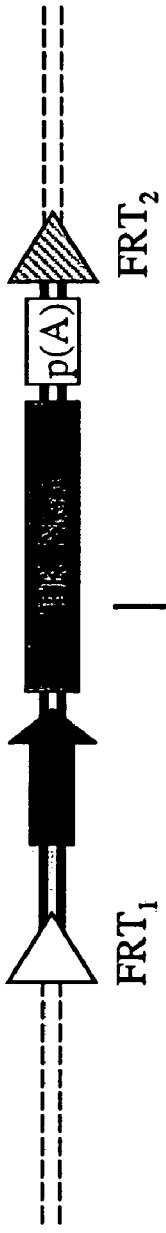
FIGS. 4A-C are schematic representations showing introduction of reporter elements and a FLP-expression vector.
Figure 4B:
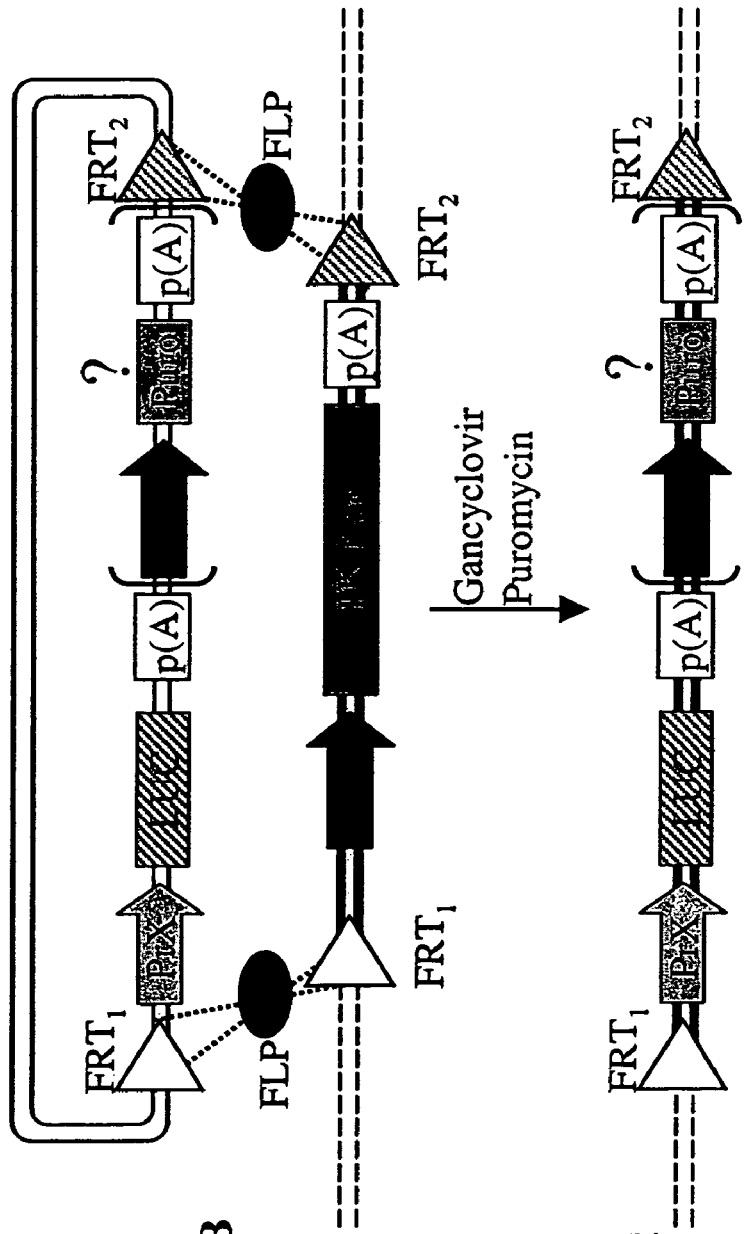
Figure 4C:
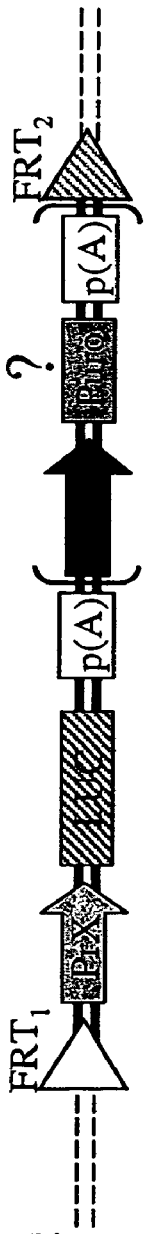

With such master "acceptor" cell lines, co-isogenic reporters of any pathway of interest can then be generated by FLP-mediated recombination and selection. Briefly, any promoter of interest can be subcloned in front of a luciferase allele. Co-transfection of such an "entry" vector, along with an expression vector encoding FLP recombinase, results in recombination at the genomic "acceptor" site bounded by FRT sites, resulting in replacement of the PGK-TK-Neo cassette with the promoter of interest driving luciferase (FIGS. 4A-C). Shown is the introduction of reporter elements and a FLP-expression vector by transient transfection (FIG. 4A). FLP mediated recombination between homologous FRT sites (FIG. 4B) followed by selection with gancyclovir results in (FIG. 4C) selection of cells in which the positive-negative TK-Neo cassette is replaced by the reporter elements in the "entry" vector. If recombination between heterologous FRT sites is a problem, a distinct selectable marker can be included in the "entry" vector.

Since FLP-mediated recombination is believed site specific, transfection and selection can even be accomplished in a population of cells, since a large proportion of the resulting recombinants likely yield the same product.

To minimize recombination between the heterologous FRT sites situated in cis—(i.e., recombination between $FRT_1$ and $FRT_2$), a unique, selectable marker in the incoming vector of interest can be used (FIGS. 4B-C).

This approach allows for the ability to rapidly generate any number of co-isogenic reporters, differing only by the promoter of interest and not by where it is integrated in the genome, which will be constant. In fact, this approach allows for comparison of stimulus-responsive versus point mutated promoters, as the most elegant control for any pathway of interest (e.g., TCF-responsive promoter vs. same promoter with a point mutation in the cognate TCF-response element). This is accomplished through site-directed recombination, since random integration is subject to copy number and integration site variations in gene expression.

Use of the CRE/Lox recombinase system is also encompassed by the methods of the present invention.

Example 2

Figures 2A, 2B:
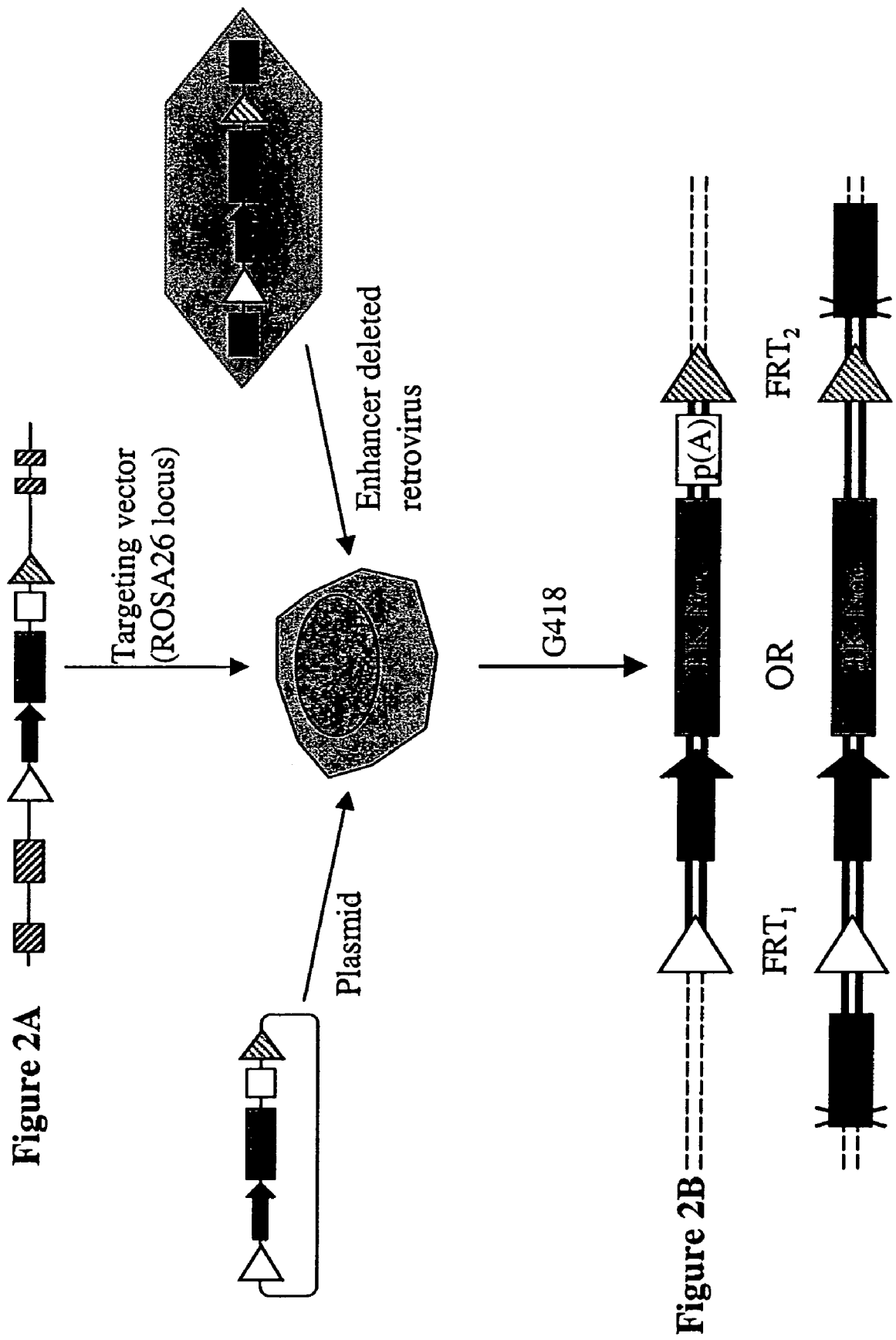
FIG. 2A is a schematic representation showing introduction at the ROSA26 locus of the FRT-flanked "acceptor" site into cells using random plasmid or retroviral integration.
FIG. 2B is a schematic representation showing an integrated TK-NEO construct integrated into an "acceptor" site consisting of a positive-negative selection cassette flanked by heterologous FRT-sites.

Construction of ES Lines with a Vector Containing a Nucleic Acid Encoding Luciferase and Neomycin Phosphotransferase for Generating Stimuli-Responsive Reporter Mice A co-isogenic reporter mouse is generated using recombinant ES cells. Transcriptional reporter mice, analogous to the reporter cell lines described in Example 1, allows for the analysis of pathway-specific transcriptional activity within the normal tissues of a host animal. The heterologous FRT-flanked acceptor cassette is introduced into the ROSA26 locus as shown in FIG. 2A. A relatively weak promoter such as the ROSA promoter is preferred for this construct, as the level of luciferase expression driven by the ROSA26 promoter is insufficient to be visualized. In fact, the knock-in strategy as shown allows for the removal of the promoter elements that have been shown important for transcription from the ROSA26 locus, thus further attenuating endogenous promoter activity. Consequently, substitution of a specific, stimulus-responsive promoter at the ROSA promoter site results in reporter activity that is predominantly a reflection of the heterologous promoter introduced into the locus and not of the ROSA promoter.

Figure 5:
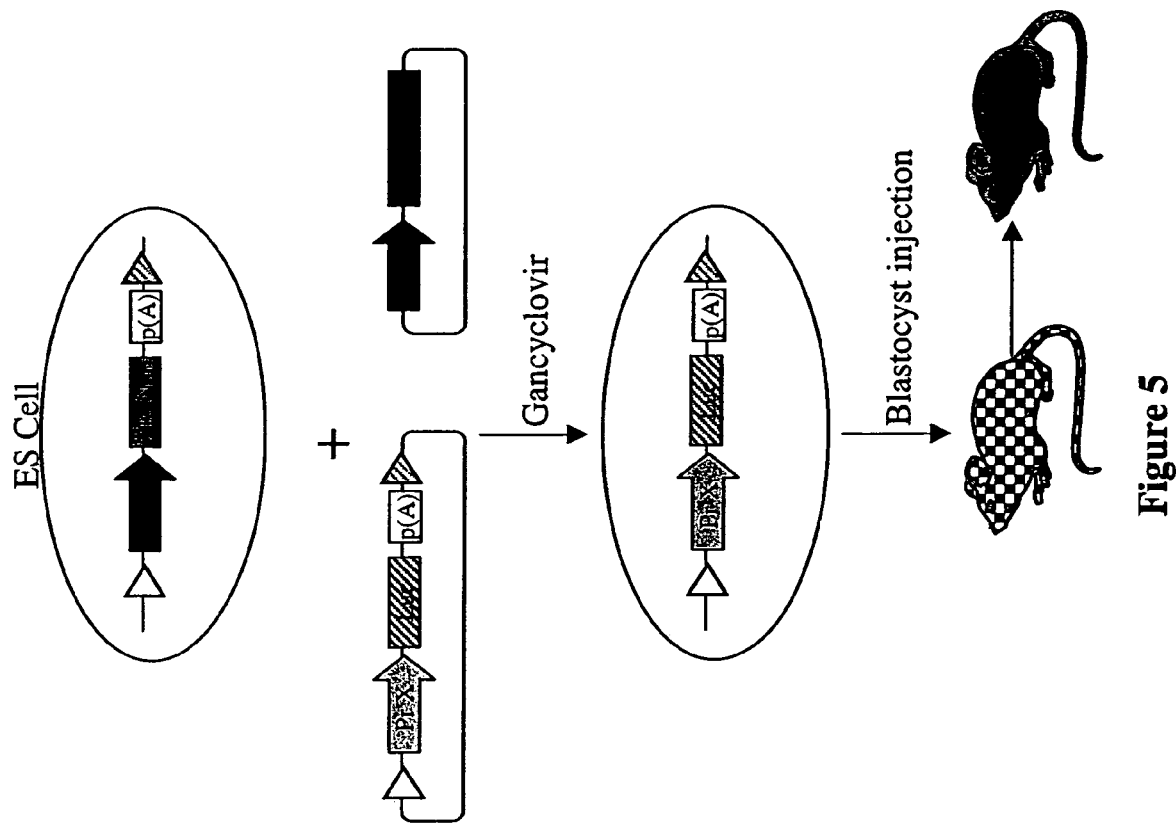
FIG. 5 is a schematic representation of a transgenic mouse created using FLP-mediated recombination.
Figure 6:
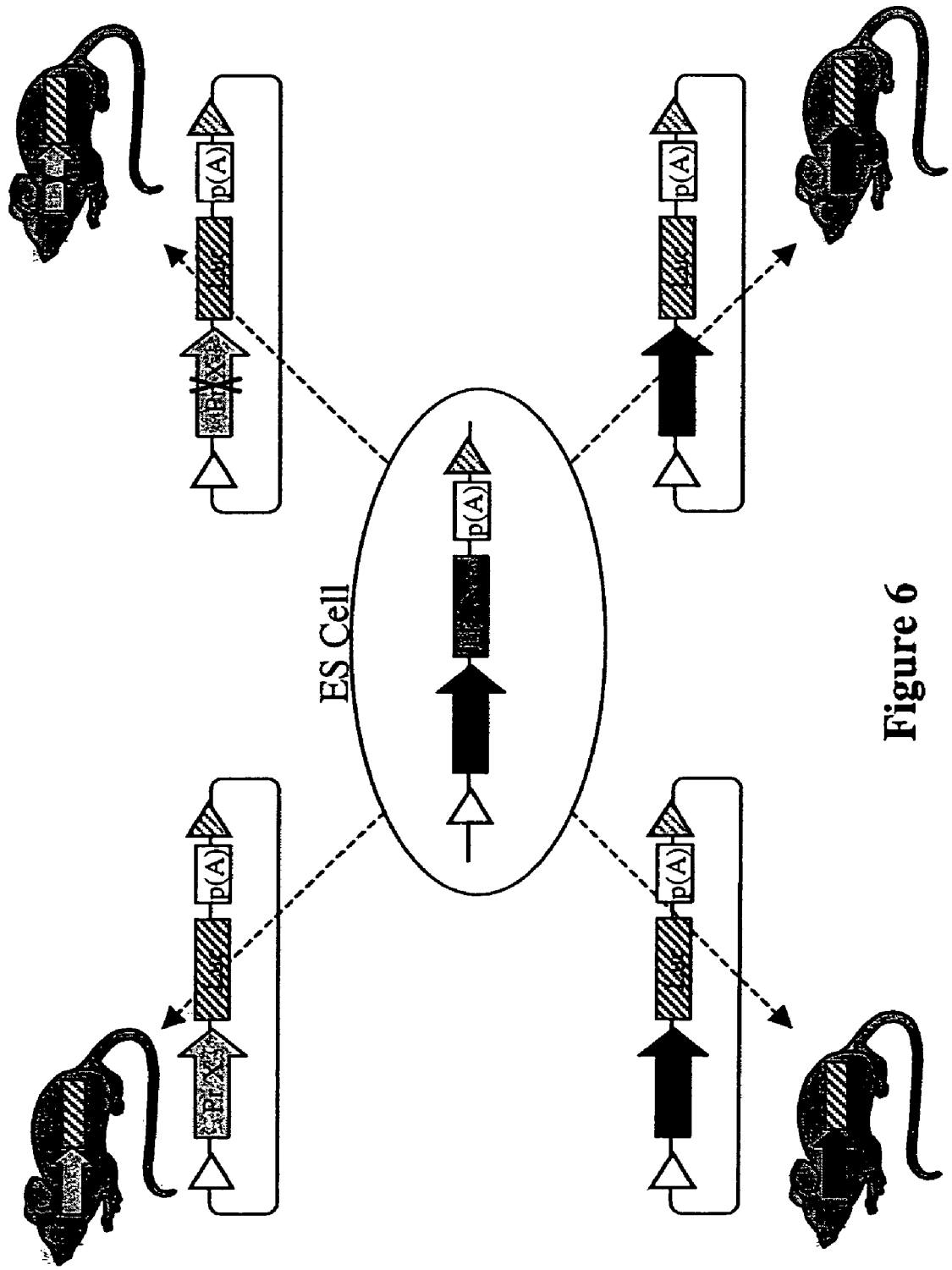
FIG. 6 is a schematic illustration showing the generation of multiple co-isogenic reporter mice using FLP-mediated recombination into a master "acceptor" ES cell.

Once a master ES clone with the FRT-flanked "acceptor" site is identified, reporter elements are introduced by FLP-mediated recombination as described in FIG. 4. Blastocyst injection of such a recombinant ES cell results in the generation of chimeric mice (FIG. 5). When crossed with 129 mice (same strain as the ES cells), the result is a reporter mouse that is co-isogenic to inbred 129 mice. By generating multiple promoter/recombinant animals from the same master ES clone, such a group of animals will be co-isogenic with their respective ectopic promoter-reporter alleles located at the same genomic site. This approach is much more expedient than knocking in a reporter transgene into the ROSA26 locus for each new targeting construct.

This approach also allows for the generation of animals in which luciferase is driven by lineage-specific promoters. For example, a series of angiogenesis-specific reporter animals can be generated by introducing various endothelial-specific promoters driving luciferase.

Example 3

Figure 7B:
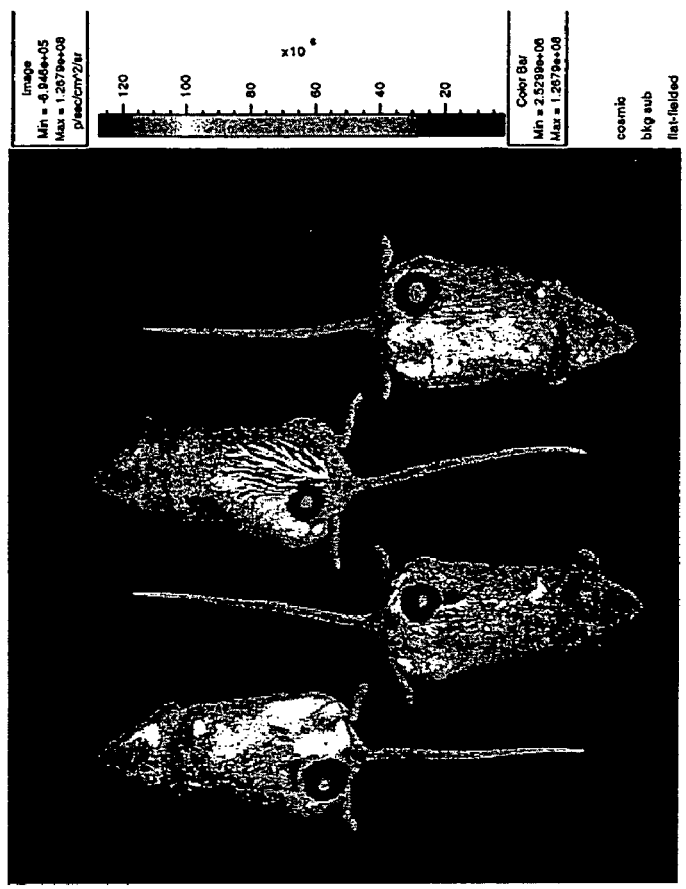
FIG. 7B is a pictorial representation showing the detection of luciferase following implanting of MDA-MB231 cells into the inguinal mammary fat pad of NOD-SCID mice, and imaged 1 week after implantation.
Figure 7A:
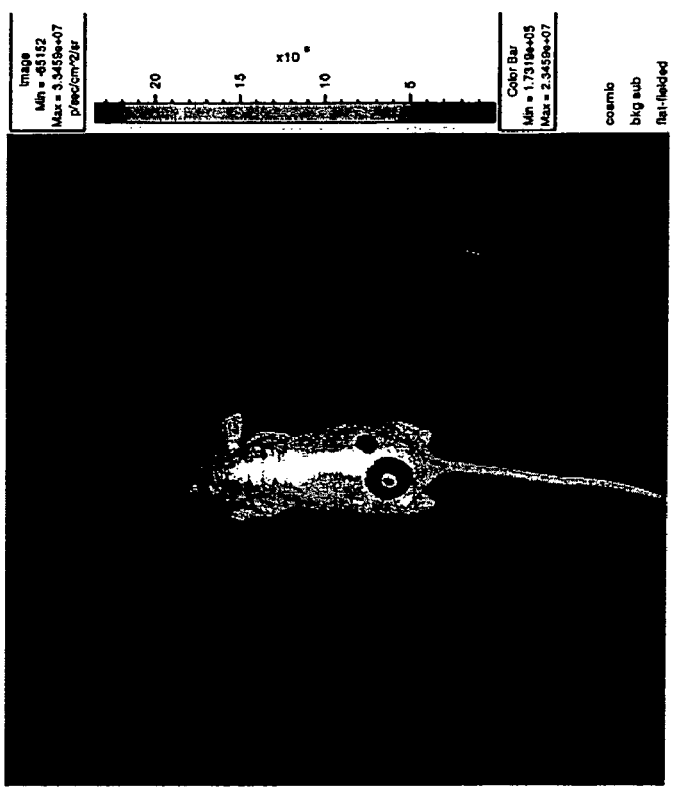
FIG. 7A is a pictorial representation showing the detection of luciferase following inoculation of MDA-MB231 cells infected with retrovirus encoding a fusion of luciferase and neomycin phosphotransferase (pMMP-LucNeo) inoculated subcutaneously in an athymic nude mouse, and imaged 48 hrs later.

Detection of Tumor Cells in Mice Using Retroviruses Encoding Luciferase—Orthotopic Implantation MDA-MB231 cells infected with retroviruses encoding a fusion of firefly luciferase and neomycin phosphotransferase were implanted subcutaneously in an athymic nude mouse, and imaged 48 hours later (FIGS. 7A and 7B). FIG. 7A shows various quantities of tumor cells implanted. As few as 10000 tumor cells could be detected. FIG. 7B demonstrates results after $10^6$ cells were implanted into the inguinal mammary fat pad of NOD-SCID mice, and imaged one week after implantation.

Figure 8:
FIG. 8 is a pictorial representation showing orthotopic brain tumor model. Mice were implanted with 50,000 U87-Luc cells. Detection was monitored over a three week period.
Figure 8:
Figure 8:

Nude mice were implanted with 50,000 U87-Luc cells. Mice were anesthetized and imaged 5 and 21 days after implantation. Absolute photonic flux over a 2 minute imaging interval is indicated by the false color. Detection of tumor cells was evident at 5 days post implantation (FIG. 8). Over a three-week time, there was a linear increase in site-specific bioluminescence intensity. This type of real-time visualization of a brain tumor allows dynamic quantification of intracranial tumor burden without performing MRI, CT scans, or similar imaging techniques.

Figure 23:
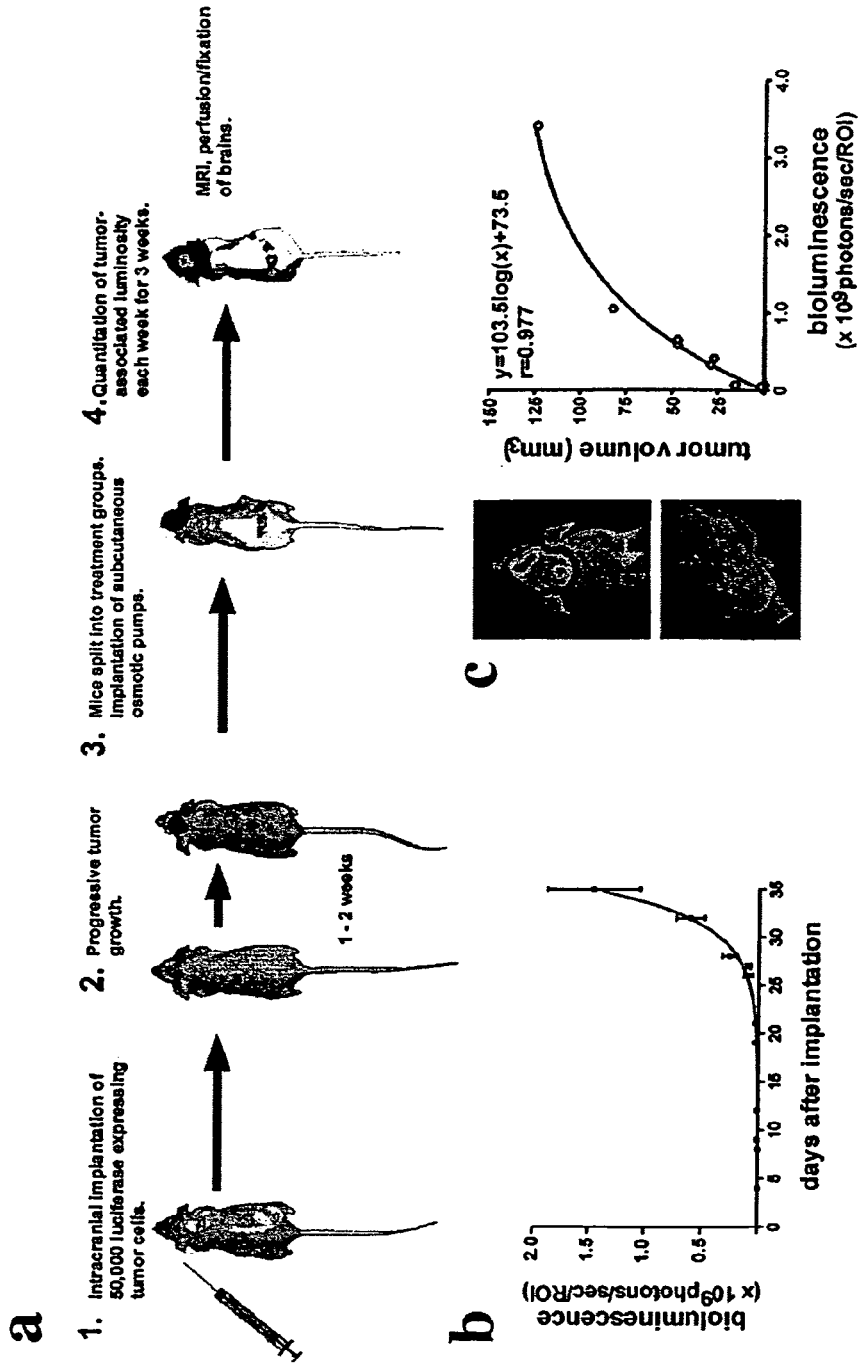
FIG. 23 is a schematic illustration showing that the imaging methods of the invention are useful in visualizing the progression of intracranial brain tumors in a mouse model.
Figure 24:
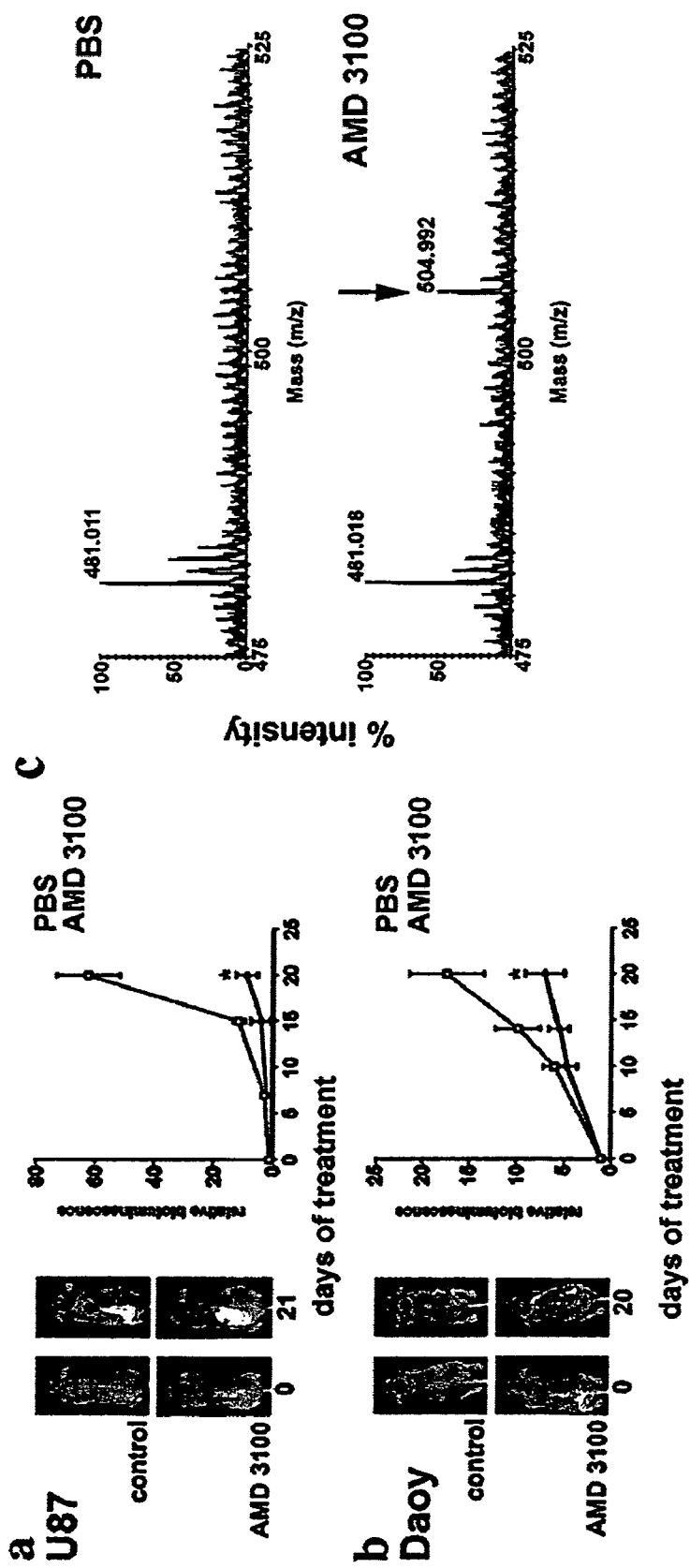
FIG. 24 is a representation showing the results of an in vivo validation of AMD-3100 (AnorMed), an inhibitor of CXCR4, in orthotopic models of GBM (U87 cells) and medulloblastoma (Daoy cells).

The validity of in vivo imaging for assessing intracranial tumor burden was evaluated by following normal growth kinetics, and by direct comparison with MRI volumetric measurements. Tumor bioluminescence was found to increase exponenetially, as expected, and was highly correlated with MRI volumetric measurements (FIG. 23), thereby fully validating in vivo imaging for orthotopic tumor burden determination. This approach can be used to rapidly assess in vivo efficacy of brain-tumor directed therapies, as was done with the CXCR4 inhibitor AMD3100 as therapy against intracranial gliomas and medulloblastomas (FIG. 24).

Example 4

Cell Imaging Following Engraftment of Hematologic Cancer Cells in Vivo

Figure 9B:
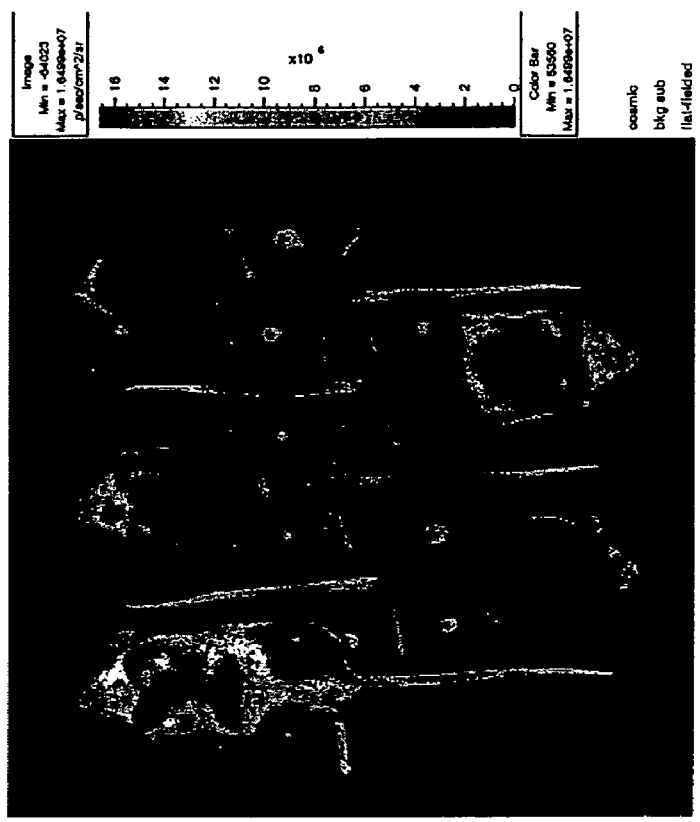
FIGS. 9A-B are pictorial representations of RS(4;11) acute lymphocytic leukemia cells labeled with pMMP-LucNeo 4 days (FIG. 9A) and 14 days following intravenous injection into SCID-beige mice (FIG. 9B).
Figure 9A:
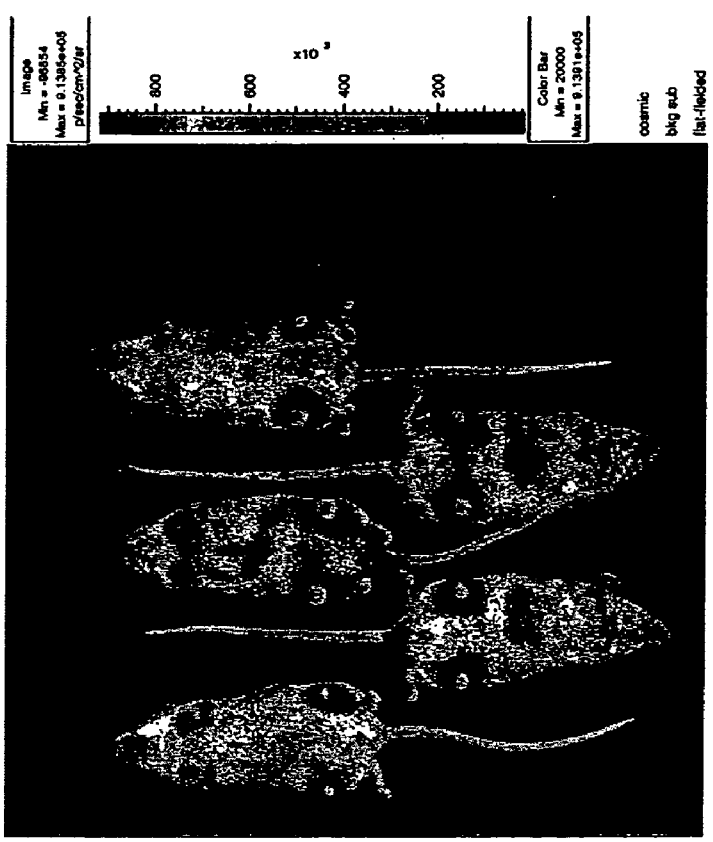

The fate of engrafted leukemic cells was examined by measuring light emission. The pMMP-LucNeo construct was introduced into RS(4;11) acute lymphocytic leukemia cells. $10^6$ of the transduced cells were intravenously injected into SCID-beige mice. Leukemic cells were detected by detecting emitted light. The results are shown in FIGS. 9A and 9B. Engraftment of leukemia cells into the femurs was evident by 4 days after injection (FIG. 9A). After 14 days, there was a linear increase in total body bioluminescence with diffuse signal by 2 weeks post-inoculation (FIG. 9B). Note the scale in the right panel is 10× that on the left.

Engraftment of leukemia cells in bone marrow, liver, and spleen was evident as early as 4 days after injection (FIG. 9A). Engraftment of leukemia cells into the femurs was evident by 4 days after injection. Over time, there was a linear increase in total body bioluminescence with diffuse signal by 2 weeks post-inoculation. (FIG. 9B)

These results demonstrate that exogeneously introduced ppMP-luc-neo cells can be used to follow the engraftment and proliferation of cells in a mammalian host, as shown in FIGS. 15, 16 19, 20, 21, and 22.

Example 5

Cell Imaging of Metastatic Disease

The progression of metastatic disease was followed using pMMP-LucNeo labeled MDA-MB231 cells. $10^6$ pMMP-LucNeo labeled MDA-MB231 cells were injected intravenously into nude mice. The control mouse was not inoculated with tumor cells.

Figure 10:
FIG. 10 is a pictorial representation of metastases following intravenous injection of $10^6$ pMMP-LucNeo labeled MDA-MB231 cells into nude mice.

The results are shown in FIG. 10. Metastatic nodules were apparent within two weeks, and were easily imaged in vivo. Using this technology, it is possible to investigate the efficacy of anti-metastatic therapies.

Example 6

Figure 25:
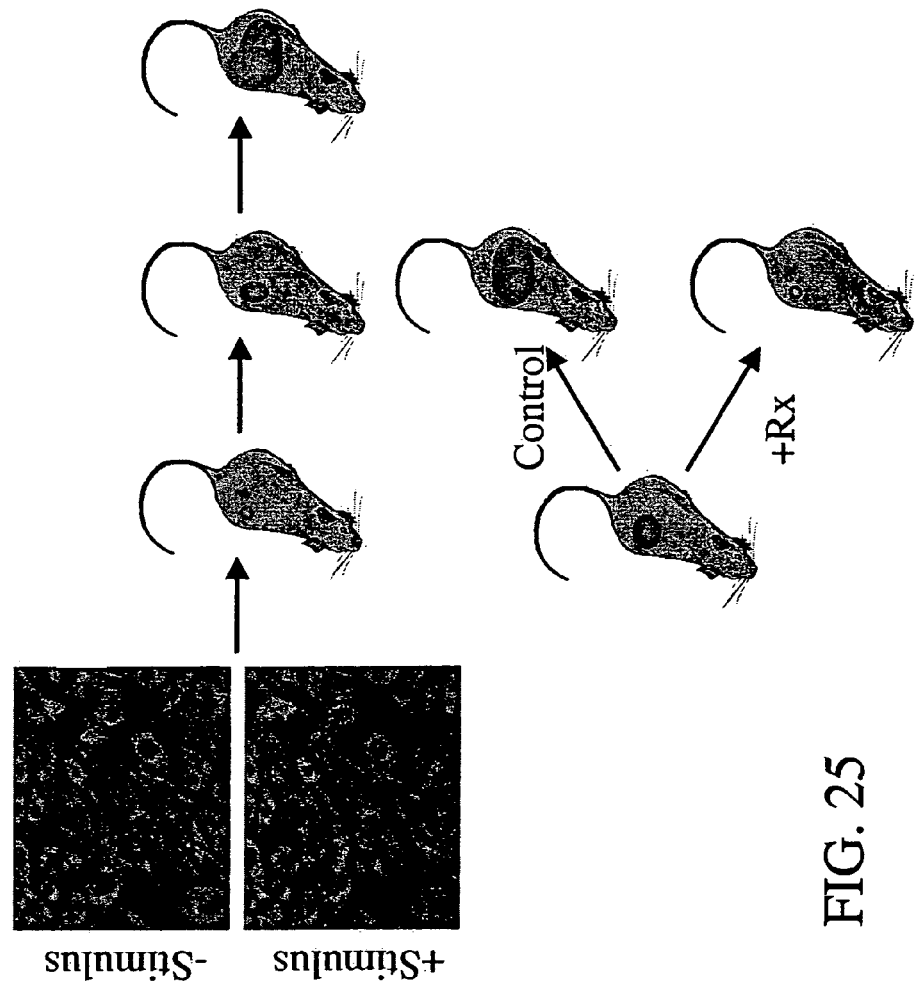
FIG. 25 is a schematic illustration showing the use of reporter cells to evaluate the activity of signal transduction pathways in vivo and to determine the activity of a test agent (+Rx).

Assessment of the Effectiveness of Drugs Targeted to Specific Signaling Transduction Pathways Within Evolving Tumor Masses In principle, reporter cells could be generated for any signal transduction pathway in which activation or suppression results in a downstream change in transcriptional activity, e.g., as determined by global expression profiling. Identification of a cis-acting element that drives expression of luciferase in a stimulus-specific manner can be used to generate reporter cell lines that can indicate the activity of the given transcriptional pathway in vivo (FIG. 25). In the case of a targeted therapeutic designed to attenuate a given signal transduction pathway, such reporter cells can be used to verify that the therapeutic indeed targets the pathway of interest in vivo (FIG. 25).

Figure 27:
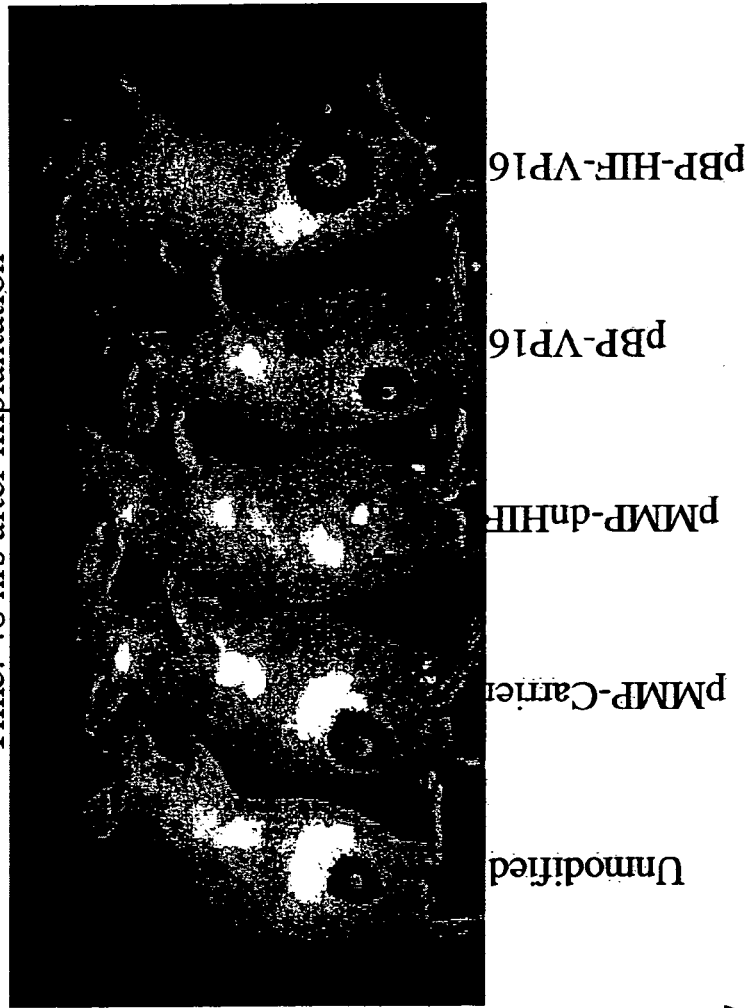
FIG. 27 is a pictorial illustration demonstrating the use of a hypoxia-inducible in vivo model system. A HepG2 tumor cell line is contacted with an erythropoietin-luciferase(EPO-Luc c.1) construct and innoculatd into an appropriate strain of mice. A detectable signal is appropriately attenuated by a dominant-negative polypeptide (pMMP-dnHIF), and super-activated by a dominant-positive allele of HIF-1a (pBP-HF-VP16). In contrast, vector controls (pMMP-carrier, pBP-VP16) had no effect on signal, thus validating this cell line for imaging the activity of the hypoxia-inducible factor (HIF) pathway in vivo.

The efficacy of drugs targeting specific-signal transduction pathways within evolving tumor masses can be followed and quantified in vivo. A reporter cell line in which luciferase is expressed under hypoxic conditions was created stably transfecting HepG2 cells with a construct composed of the erythropoietin enhancer element driving the expression of luciferase (HepG2-Epo-Luc). This reporter cell line was validated by infecting aliquots with retroviruses encoding a dominant-negative (dnHIF) or dominant-positive (HIF-VP16) modulator of hypoxia-inducible transcription, and demonstrating a respective decrement and increase in reporter activity in vivo (FIG. 27).

Figure 11:
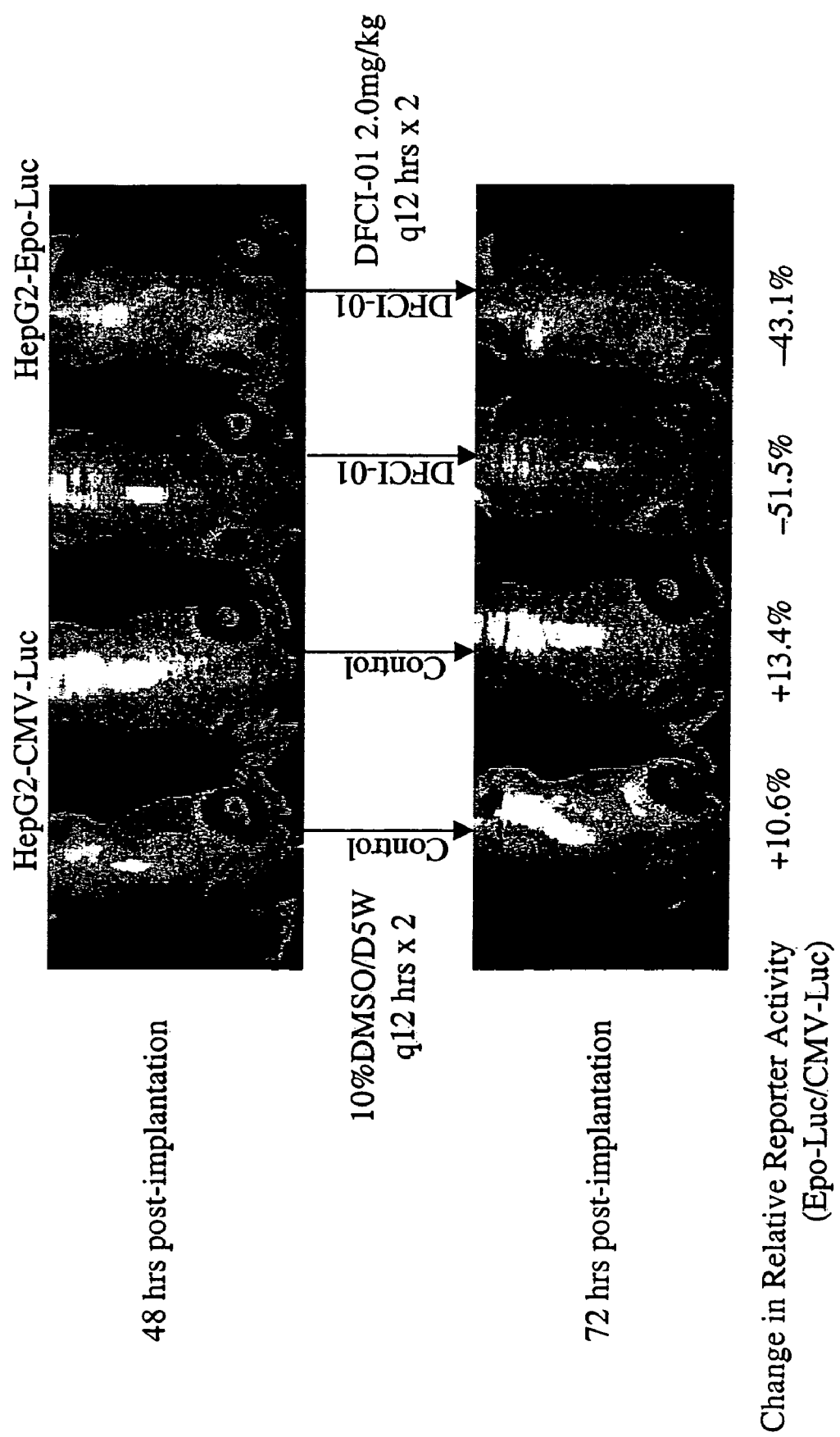
FIG. 11 is a pictorial representation showing quantification of the activity of signal transduction pathways 48 hours and 72 hours after implanting into nude mice $10^6$ hypoxia reporter cells (HepG2-Epo-Luc) and a control constitutive luciferase expressing cell line (HepG2-CMV-Luc).

Nude mice were implanted with $10^6$ hypoxia reporter cells (HepG2-Epo-Luc) and a control constitutive luciferase expressing cell line (HepG2-CMV-Luc). Animals were imaged after 48 hours, then treated with 2 doses of a compound that blocks hypoxia-inducible transcription (DFCI-01 or PKF-116) or vehicle control. Animals were imaged again 72 hours after implanting cells. Reimaging revealed specific attenuation of hypoxia-inducible transcription (FIG. 11).

Figure 26:
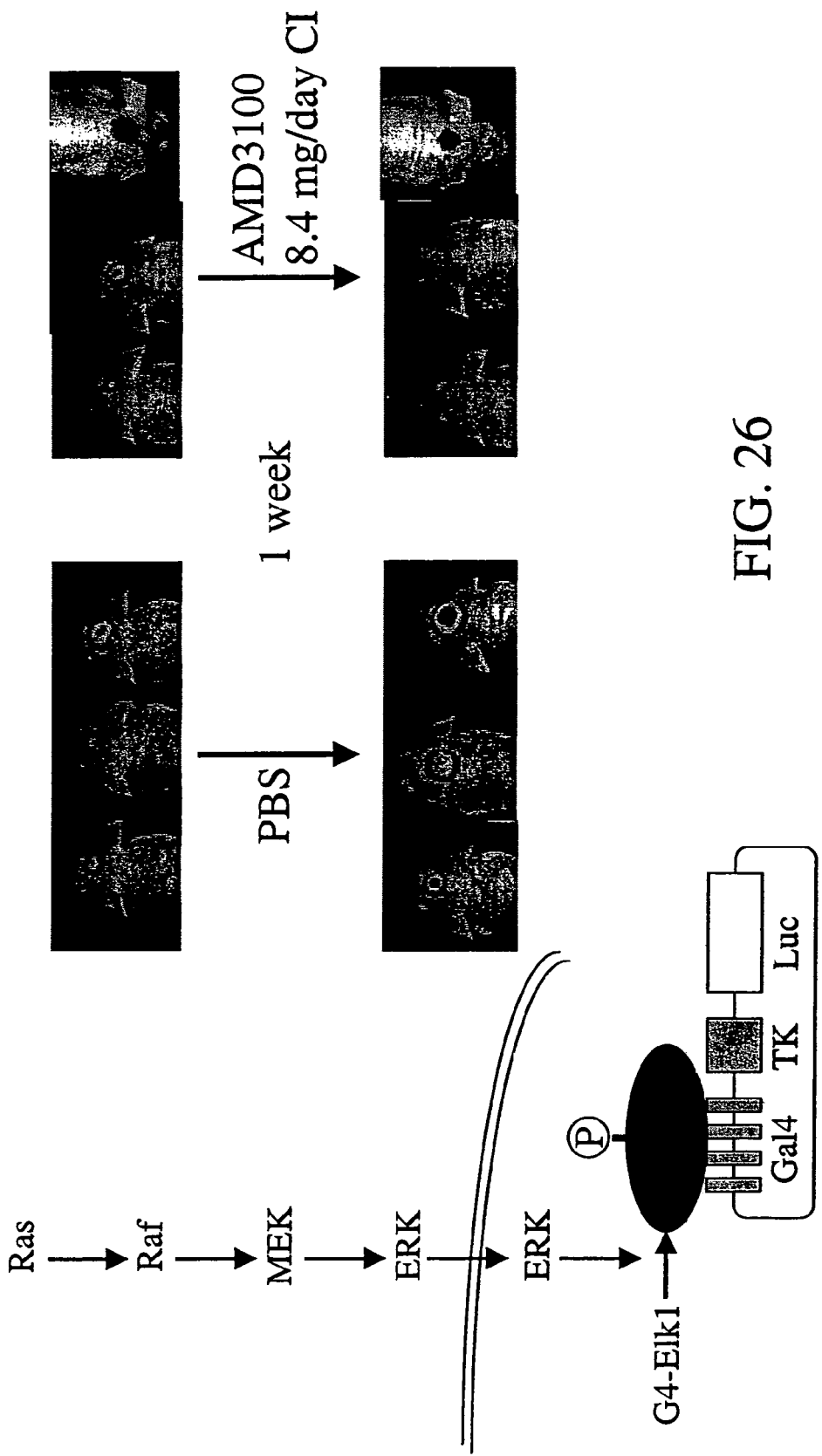
FIG. 26 is a schematic illustration illustrating the validation of AMD3100 as an inhibitor of the ERK1/2 signaling pathway in vivo.

In separate studies, nude mice were implanted with 32D/BCR-ABL cells. Animals were imaged, then treated with a compound that has been found to have possible effects on treating some types of cancer (STI-571) or vehicle control. Reimaging revealed that the drug had a positive effect on reducing the bioluminescence intensity as compared with controls. In separate studies, nude mice were implanted with TS(4;11)-LucNeo cells. Animals were imaged, then treated with an anti-angiogenesis agent (PKC-412) at 150 mg/kg/day or control. Reimaging revealed that the administration of drug over a two week period resulted in constant bioluminescent flux as compared to controls in which the flux increased over the same time-period In a second example, a cell line was created that reported on the activity of the Ras/Raf pathway (FIG. 26). These cells were used to evaluate the activity of the Ras/Raf pathway in an orthotopic brain tumor model. Using a small molecule inhibitor of the CXCR4 chemokine receptor, treatment of animals revealed that AMD3100 attenuated the Ras/Raf pathway in vivo (FIG. 26), consistent with changes suggested by conventional histopathological evaluation.

These results demonstrate that a LucNeo construct can be used to detect changes in the activity of an operably linked inducible reporter.

Example 7

Figure 12:
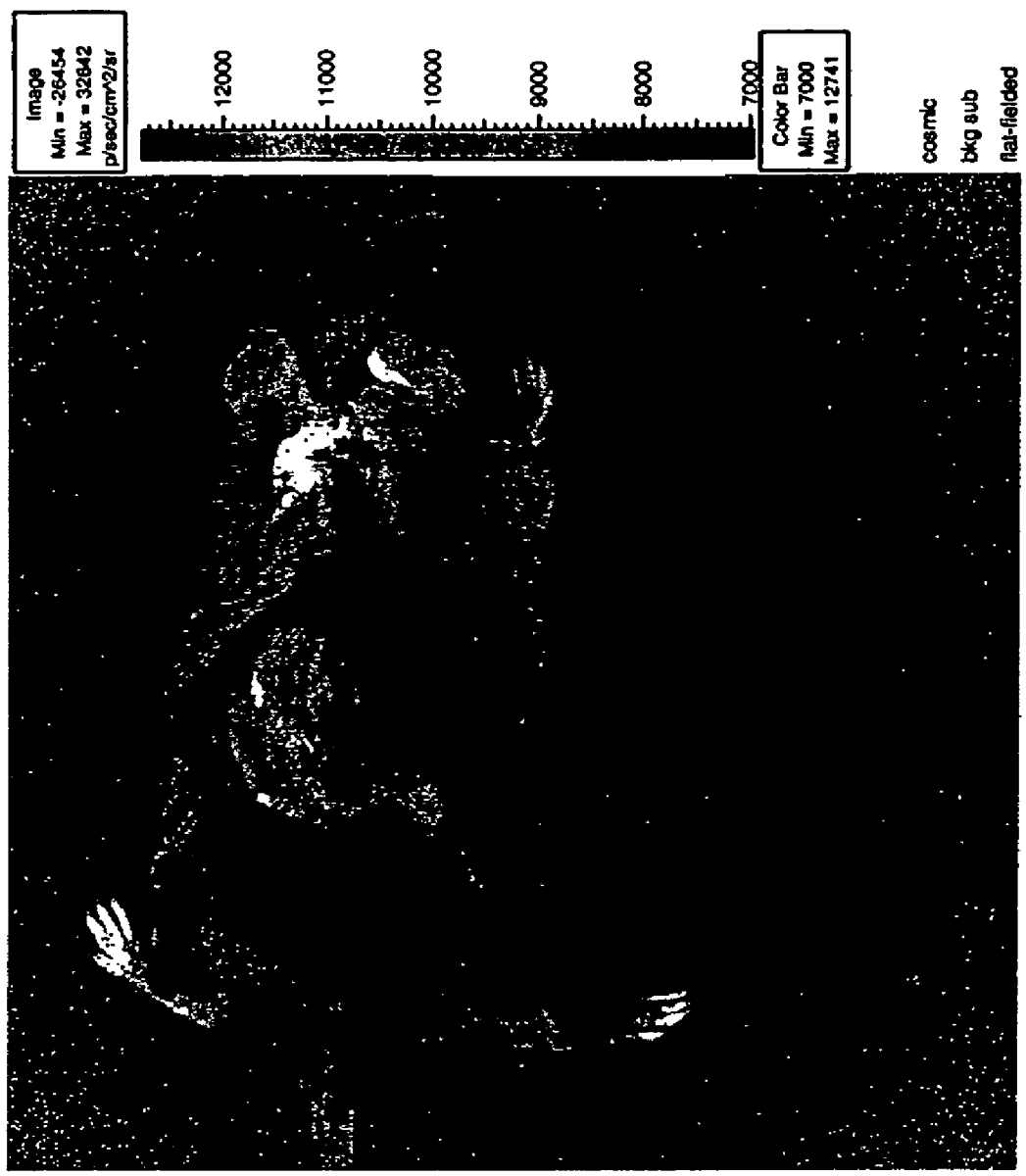
FIG. 12 is a pictorial representation showing the assessment of transgenic mice expressing luciferase from the Ang-2 promoter.

Assessment of Transgenic Mice Expressing Luciferase from the Ang-2 Promoter, a Highly Restricted Proliferating Endothelial Cell-Specific Promoter A transgenic mouse model was created with luciferase expressed from promoters active in proliferating endothelial cells. Transgenic mice were created by pronuclear injection of a transgene containing a luciferase gene under the control of an Ang-2 promoter. A wound was made in the mouse, and strong bioluminescence was detected at the site of the wound. The results are shown in FIG. 12. The results indicate the Ang-2 transgene promoter is operating in a tissue-specific manner.

Figure 13:
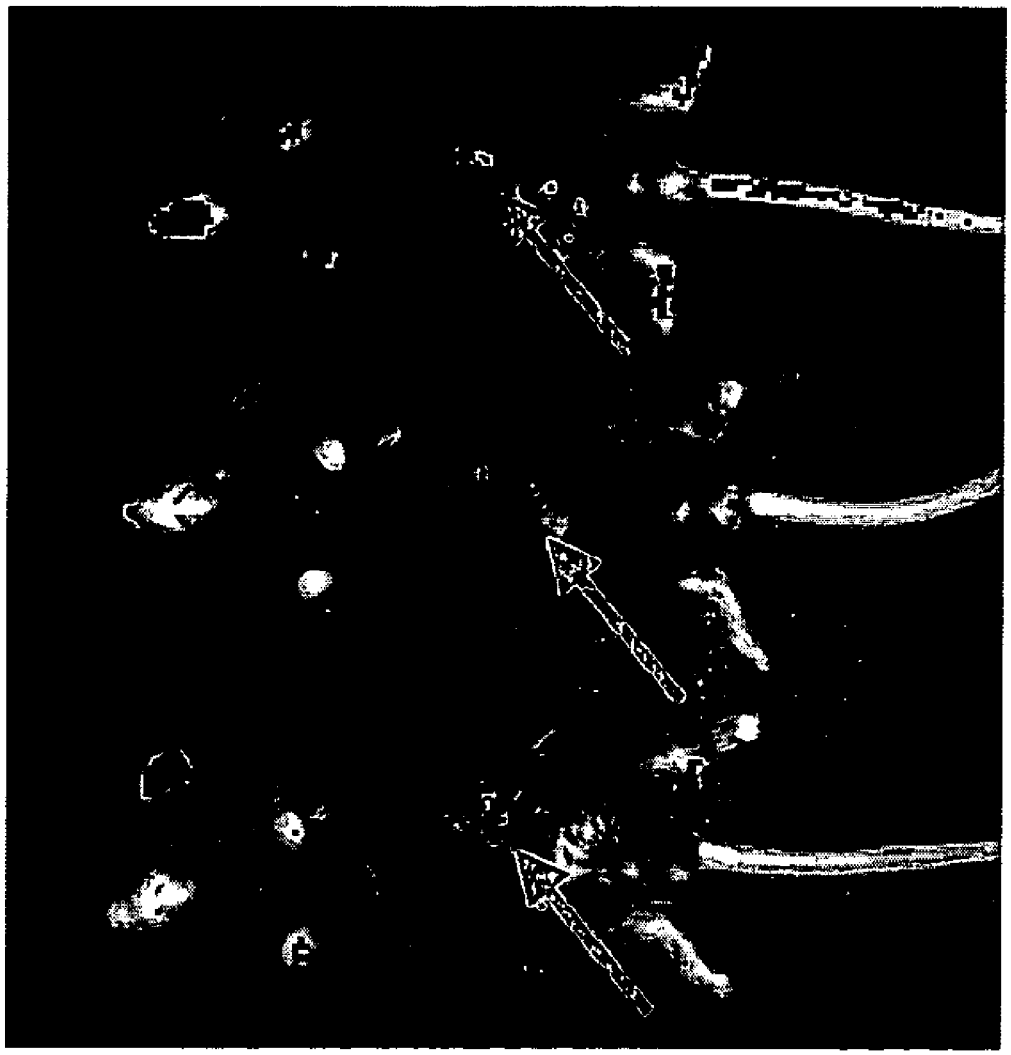
FIG. 13 is a pictorial representation of transgenic mice carrying the Ang-2-Luc transgene.

Three mice carrying the Ang-2-Luc transgene were injected with Matrigel with VEGF and bFGF (arrows) (FIG. 13). Mice were imaged 72 hrs after injection. Mice 1 and 3 show specific emission from sites of VEGF/bFGF implantation, and are potentially angiogenesis-specific reporter mice.

Example 8

The Ang-2 Promoter as an Endothelial Cell-Specific Promoter

The Ang-2 promoter sequence was determined by search of the mouse genome database. The nucleotide sequence of this gene is provided above.

Figure 14:
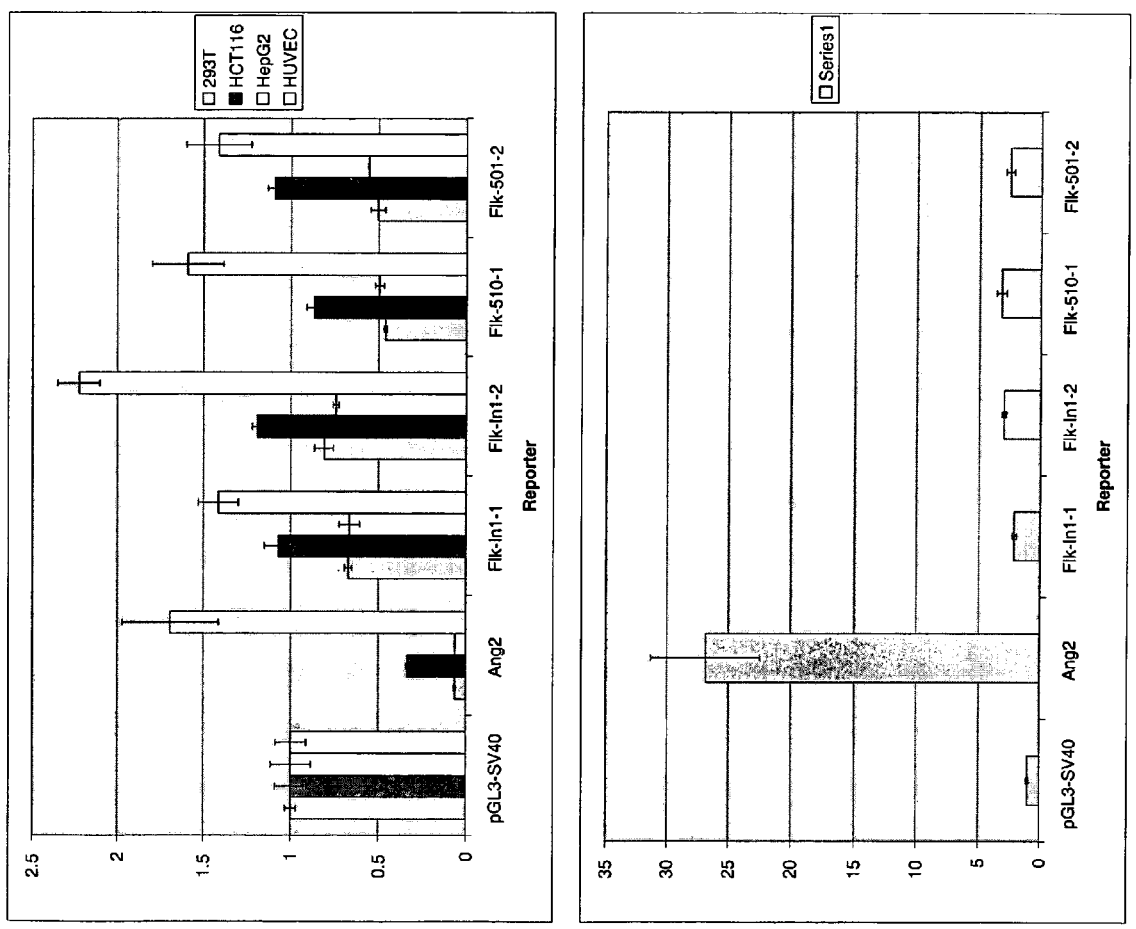
FIG. 14 is a representation of the results of expressing a construct containing the Ang-2 promoter in endothelial cells.
Figure 15:
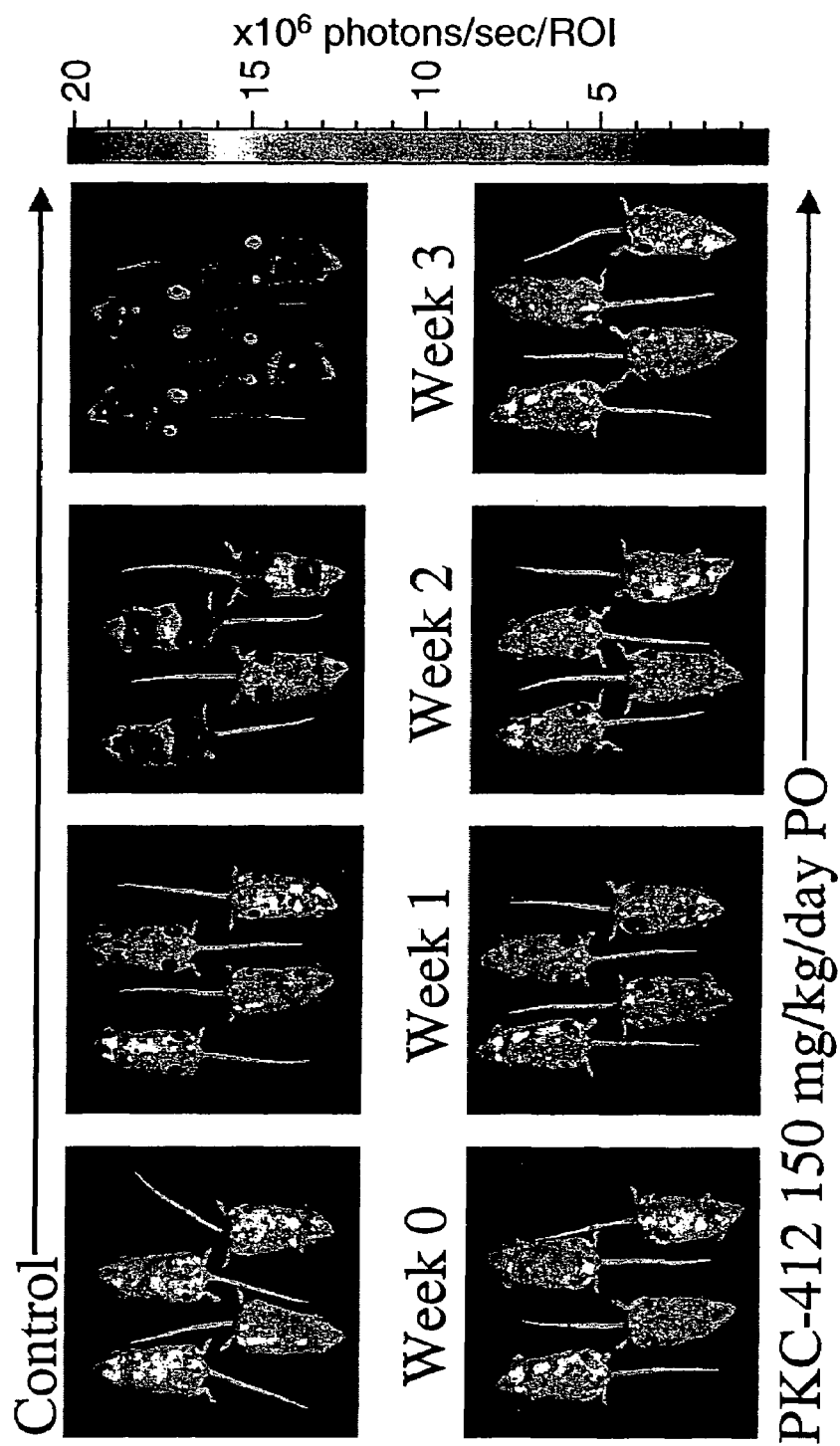
FIG. 15 is a pictorial representation of treatment of mice bearing MLL leukemia cell line TS(4;11) with the FLT3 inhibitor PKC-412.
Figure 16:
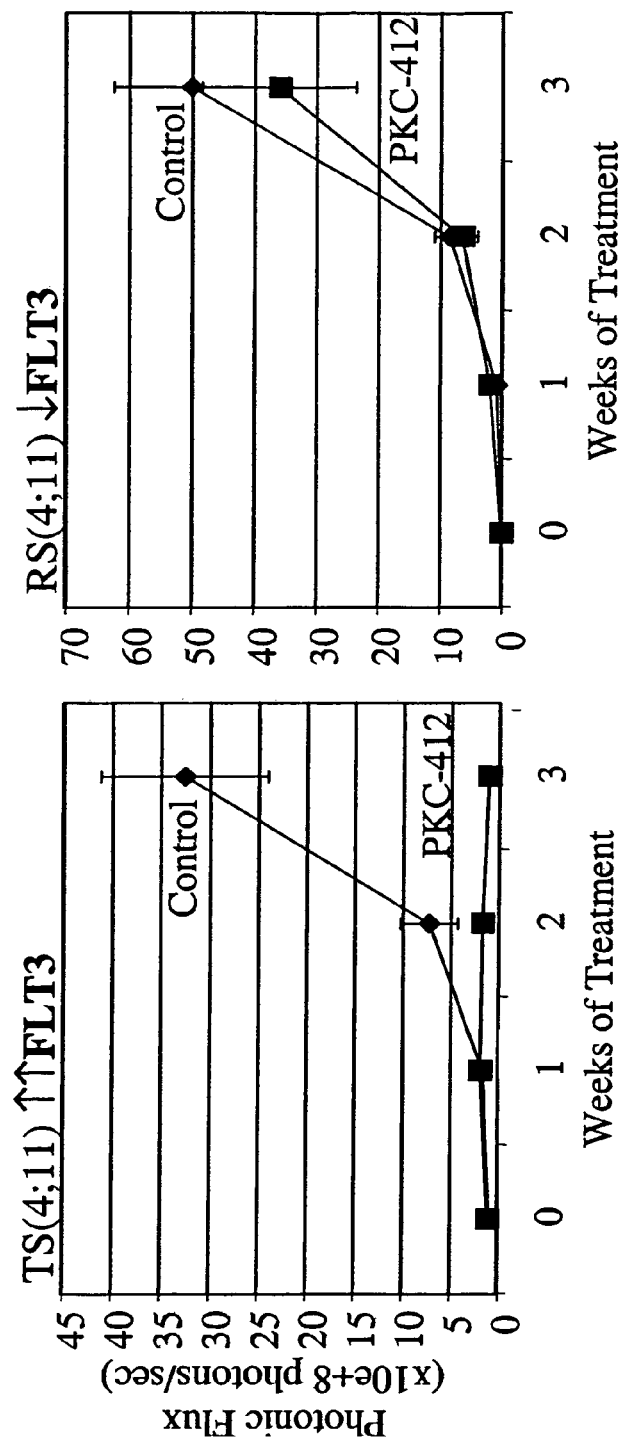
FIG. 16 is a series of graphs indicating quantitatively that the FLT3 inhibitor PKC-412 reduces tumor cell size in mice bearing TS(4;11) MLL cells (left graph) but not RS4;11) control cells (right graph).

The construct was transfected into the indicated cell lines (293T, HCT116, HepG2) and into human umbilical vein endothelial cells (HUVEC) (FIG. 14). Expression was compared to luciferase expression from an SV40 promoter. Expression was also examined from the previously described endothelial Flk promoter constructs, which are described above. The Ang-2 promoter is much more specific in comparison to Flk reporters (lower panel), when activity in endothelial cells relative to HepG2 cells (hepatoma) is compared.

Example 9

Figure 17:
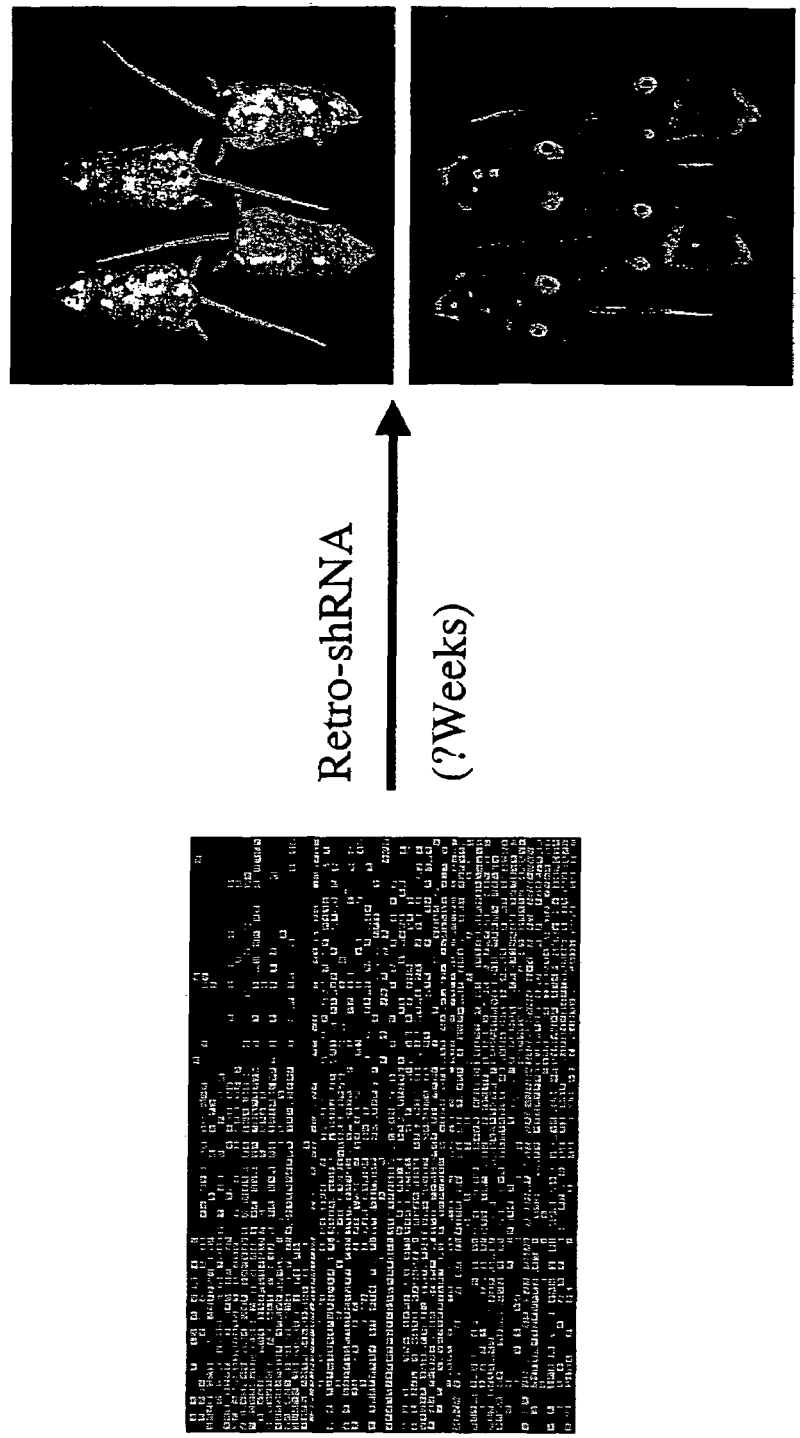
FIG. 17 is a schematic illustration of an embodiment of the invention, wherein potential components of a signaling pathway are identified (such as by gene array analysis, shown at left) and then tested using the in vivo model system (e.g., the mouse leukemia model, shown at right) using retroviruses or lentiviruses to express short hairpin RNA interference molecules targeting the potential components.
Figure 18:
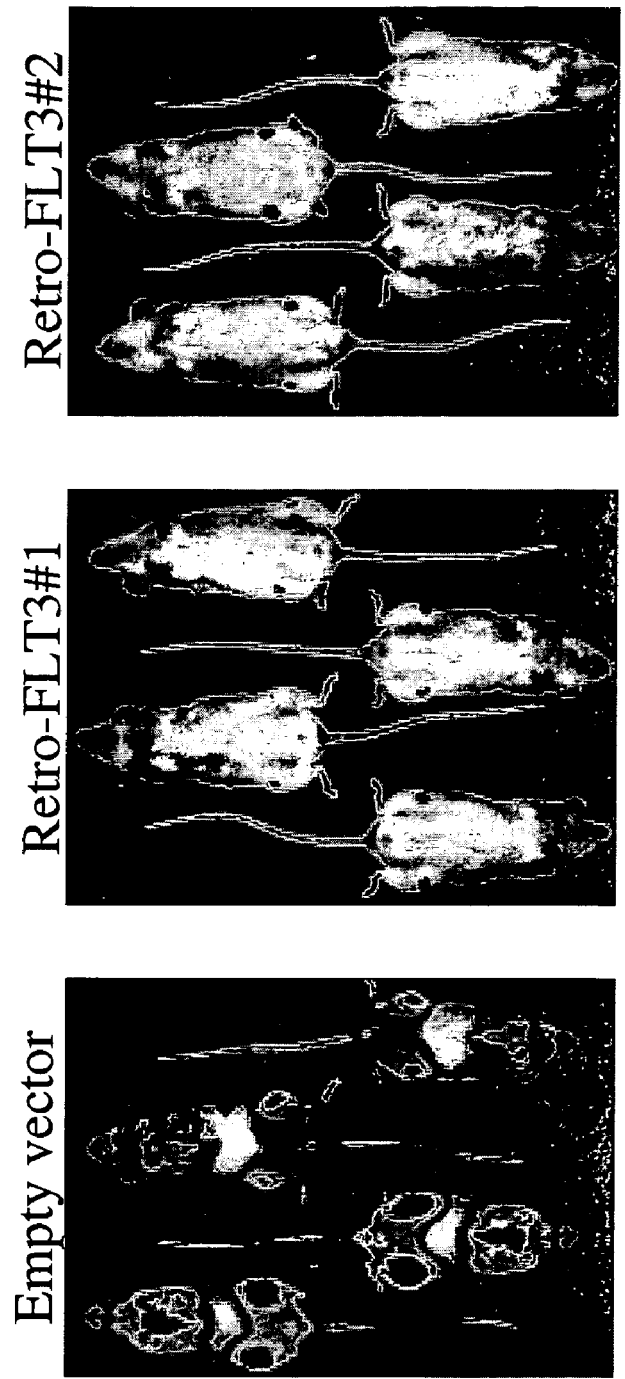
FIG. 18 is a representation showing the results of using retrovirally-targeted shRNA directed to FLT3 in a mouse leukemia model, which demonstrate a reduction vivo tumor growth.
Figure 19:
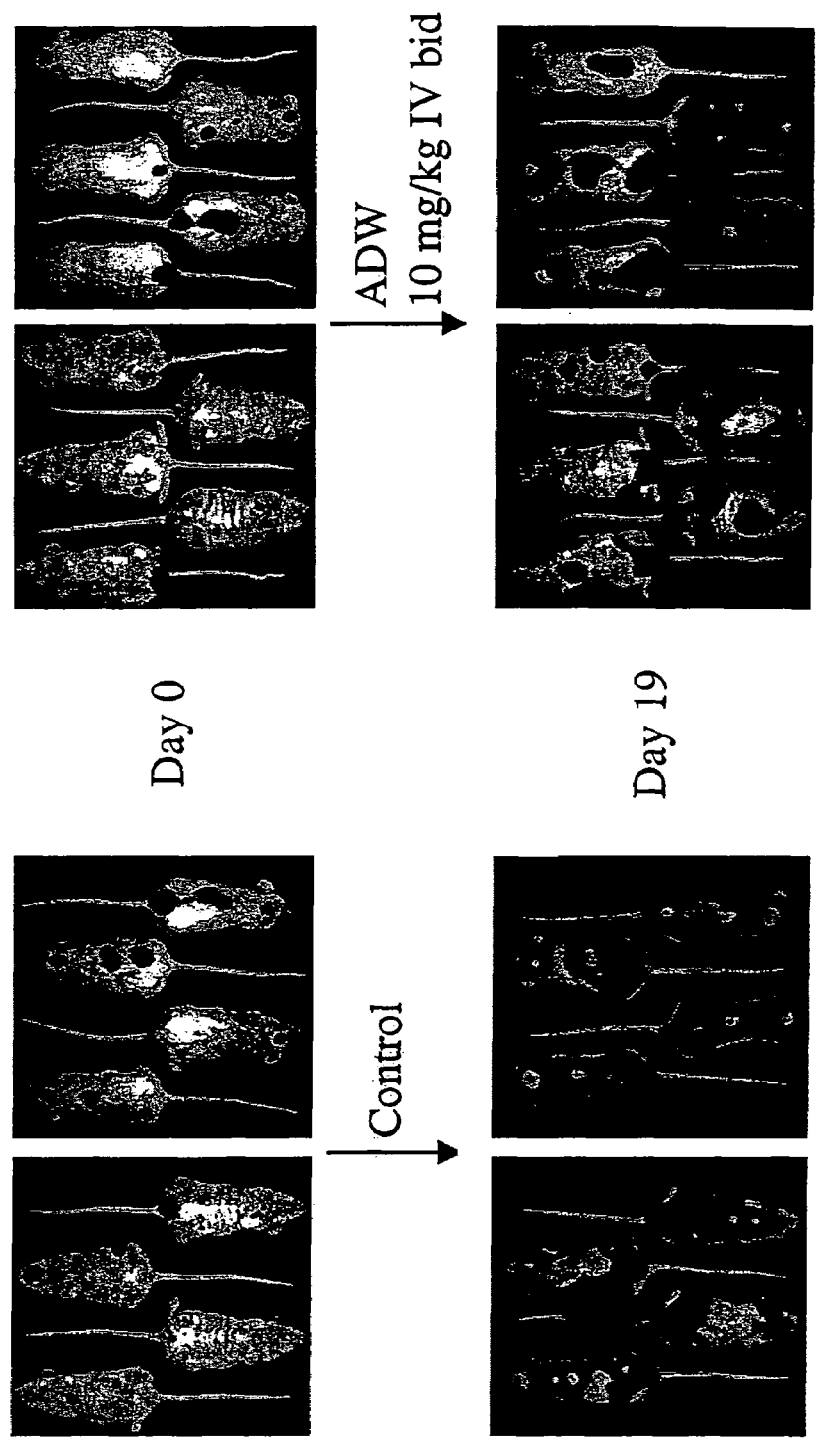
FIG. 19 is a representation of the results of generating a multiple myeloma (MM) model, that was created by selecting cells with affinity for growth in bone. This model replicates the pattern of MM growth in human patients, and was used to evaluate ADW, a novel inhibitor of IGF-1R (NVP-ADW742), by reduction of tumor burden.
Figure 20:
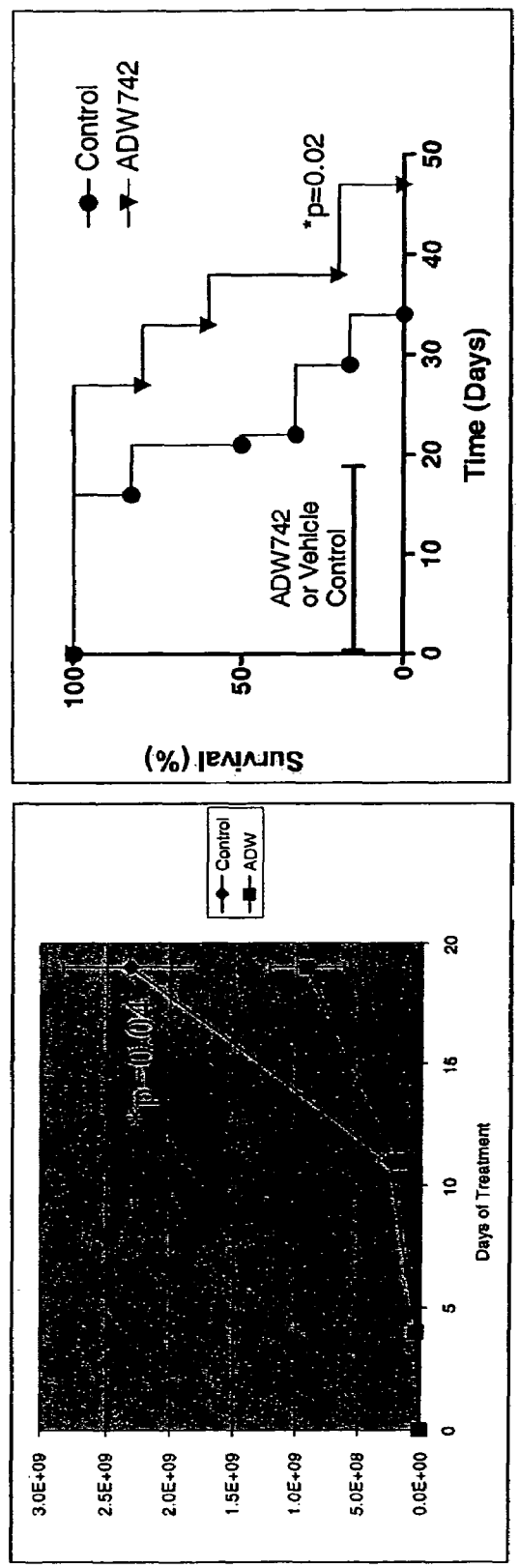
FIG. 20 is a series of graphs indicating quantitatively that the treatment with ADW is positively correlated with survival as compared to untreated control.
Figure 21:
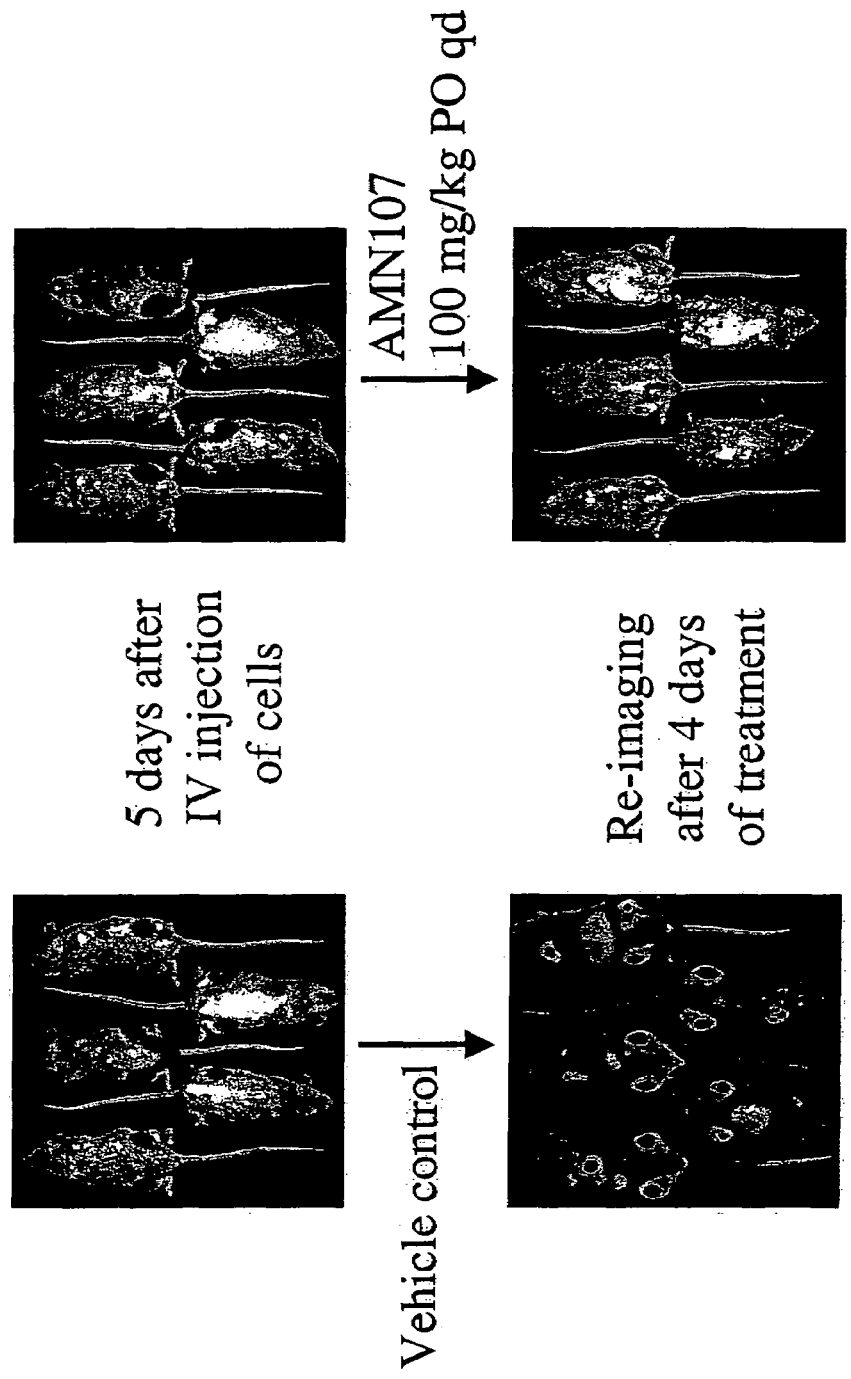
FIG. 21 is a representation showing the results of a CML model used to evaluate the ABL-inhibitor AMN107. Using this method, it was qualitatively demonstrated that AMN107 is efficacious against 32D/p210-Luc cells in vivo using only five animals over a nine day assay, which is more effective and efficient than conventional time to death studies utilizing large cohorts of mice (12-20) lasting months.
Figure 22:
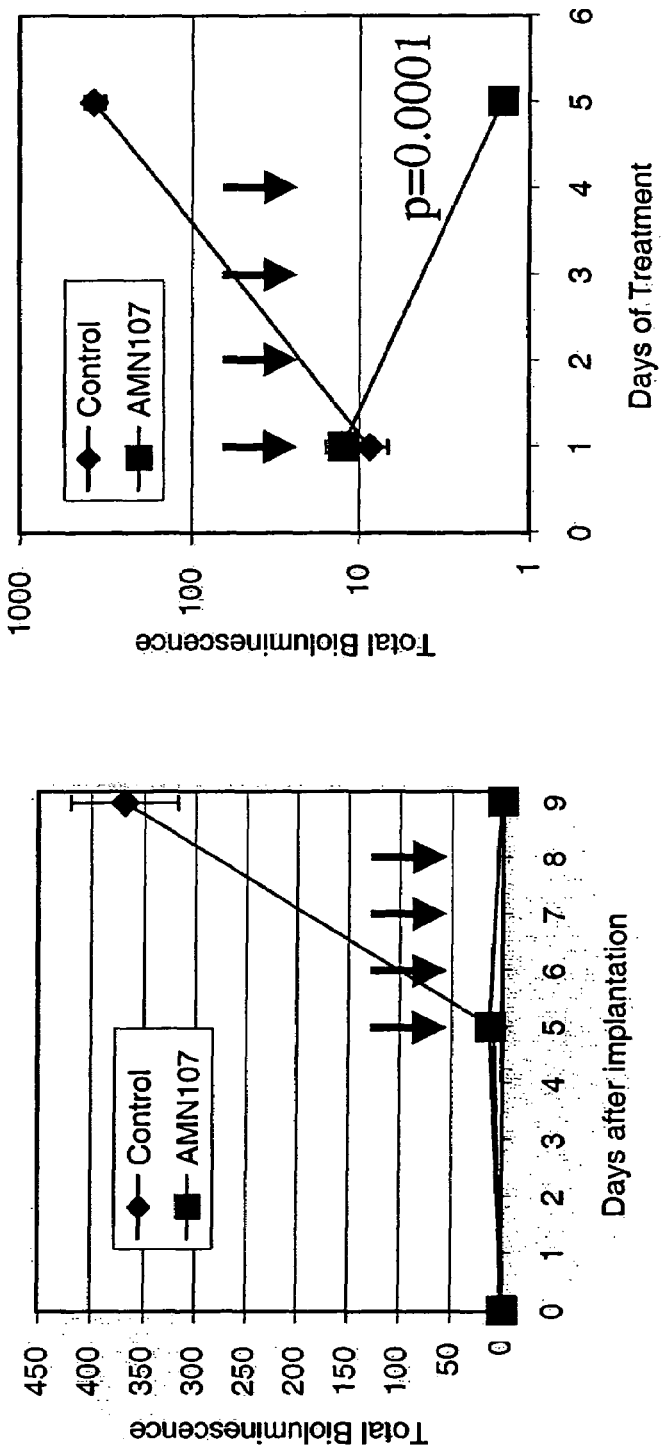
FIG. 22 is is a series of graphs quantitatively indicating that AMN107 inhibits tumor cell growth of 32D/p210-Luc cells.

Use of Transgenic Mice Expressing Luciferase to Identify Biological Components in a Signal Transduction Pathway FIG. 17 is a schematic illustration of an embodiment of the invention, wherein potential components of a signaling pathway are identified. A biological component such as a polynucleotide or polypeptide (e.g., FLT3) is identified by predictive and/or experimental means (such as by gene array analysis, proteomic array analysis, differential display, or library screening, mutation analysis, clinical epidemiology) and then tested using the in vivo model system. Here, a retrovirus expressing short hairpin RNA interference molecules (interfering RNA) that inhibit FLT3 translation is contacted with a mouse containing a MLL leukemia cell line TS(4,11) that contains a luciferase nucleic acid sequence and a regulatory element. Specific reduction of FLT3 levels by shRNA resulted in decresed in vivo leukemia growth (See FIG. 18), thereby demonstrating a critical requirement for FLT3 in driving the growth of these cells in vivo, and validating FLT3 as a novel anti-tumor target in this tumor type.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. An isolated polynucleotide comprising:
   (a) a first nucleic acid encoding a light-generating gene product operably linked to a cis-acting angiopoietin-2 (Ang-2) regulatory element, wherein said cis-acting Ang-2 regulatory element comprises the nucleic acid sequence set forth in SEQ ID NO:1; and
   (b) a second nucleic acid encoding a selectable marker, wherein said selectable marker is operably linked to a promoter, and wherein expression of said selectable marker allows for selection of said polynucleotide in a eukaryotic host.

2. The polynucleotide of claim 1, wherein said light-generating gene product is a bioluminescent gene product.

3. The polynucleotide of claim 2, wherein said bioluminescent gene product is luciferase.

4. The polynucleotide of claim 1, wherein said selectable marker is neomycin phosphotransferase.

5. A vector comprising the polynucleotide of claim 1.

6. The vector of claim 5, wherein said vector is viral vector.

7. The vector of claim 6, wherein said viral vector is a retroviral vector.

* * * * *

SEQUENCE LISTING

```
<160> NUMBER OF SEQ ID NOS: 1

<210> SEQ ID NO 1
<211> LENGTH: 1220
<212> TYPE: DNA
<213> ORGANISM: Mus musculus

<400> SEQUENCE: 1
gagtcttccc agtaccgatc tctgcagcat taacttctag tcatgaaggg gtggtgactc      60
tggaccagca gagccacaga gctggaagtg ttttagaagt cagtgcagcc cccagctttt     120
atggccaggg gcttttgaac ttaattaaaa ggggaaagtg atttgcctga gcccactgac     180
tgggactaat ttaatcagga acatgccaca gagtgatgag cccgaggaaa ccctgataca     240
```

```
gtgaaggaaa aggtgtatgt ttgtttcctc tcgacatact tcactcaaat atctattgtt      300
acttaacaga caattaatca ggccaaacca ctttaagttt tatttgtata gtattttgtg      360
ttaaggcaca gacatgtgag tgctgagaaa actgatgttg gtaacttgat ttaataatat      420
caaactgggt taaaataaaa aaaaatgtgc ataacttaaa aaaaaaacca aataccaaca      480
agactttact tccccttgga aaagcacatt tacaagggct gatcttagcc tttatattta      540
caataaagaa aataaaccaa ggtcccgata tagctgtaat tttattccta aaagaacaga      600
aactttcact atgctttaaa attaaagtga ttacctcaga tactctgcaa gcttagccta      660
caaacgagca gacagacaac agagcccag ctactctcta ggaaataatt agggtggtgc       720
ctctgacatg cccaggggtc ttgtggctgg tctgtgttcc cagaaggctt ctgcagtaca      780
cagtcctttg gggcagtaag cactatgctc tgattttcc tgttgcctgg ctagtgaccc       840
cctacaggaa gatagtgggt gagccagggg gcggagcggc tggctgcaca tgtctggctg      900
ctcttatcaa cttatcatat aagggaagga aagtgattga ttcggatact gacactgtag      960
actcagggga gaaacaaaga gtccgtgcag acctctggag tgagcagggc tgctccttcc     1020
tctcaggaca gctccgagtg tgccggggag aagagaagag aagagacagg cactgggaaa     1080
gagcctgctg cgggacggag aaggctctca ctgatggact tattcacacg gcacagccct     1140
gtgccttaga cagcagctga gagctcagga cgcaagtttg ctgaactcac agtttagaac     1200
ccaaaaagag agagagaatg                                                 1220
```